United States Patent
Holohan

(10) Patent No.: US 9,589,207 B2
(45) Date of Patent: Mar. 7, 2017

(54) JUMP SHOT AND ATHLETIC ACTIVITY ANALYSIS SYSTEM

(71) Applicant: Mo' Motion Ventures, New York, NY (US)

(72) Inventor: Maureen Holohan, Troy, NY (US)

(73) Assignee: Mo' Motion Ventures, New York, NY (US)

( * ) Notice: Subject to any disclaimer, the term of this patent is extended or adjusted under 35 U.S.C. 154(b) by 303 days.

(21) Appl. No.: 14/086,554

(22) Filed: Nov. 21, 2013

(65) Prior Publication Data
US 2015/0139502 A1 May 21, 2015

(51) Int. Cl.
| | |
|---|---|
| *G06K 9/00* | (2006.01) |
| *G06K 9/62* | (2006.01) |
| *G06T 7/00* | (2006.01) |
| *G06T 7/20* | (2006.01) |
| *G06F 19/00* | (2011.01) |
| *G09B 19/00* | (2006.01) |

(52) U.S. Cl.
CPC ....... *G06K 9/6202* (2013.01); *G06F 19/3481* (2013.01); *G06K 9/00342* (2013.01); *G06T 7/0046* (2013.01); *G06T 7/2046* (2013.01); *G09B 19/0038* (2013.01); *G06T 2207/30196* (2013.01); *H04M 2250/52* (2013.01)

(58) Field of Classification Search
CPC .................................. G06K 9/00342
See application file for complete search history.

(56) References Cited

U.S. PATENT DOCUMENTS

| | | |
|---|---|---|
| 4,337,049 A | 6/1982 | Connelly |
| 4,738,447 A | 4/1988 | Brown |
| 5,746,668 A | 5/1998 | Ochs |
| 5,846,086 A | 12/1998 | Bizzi et al. |
| 5,857,855 A | 1/1999 | Katayama |
| 5,904,484 A | 5/1999 | Burns |
| 6,095,936 A | 8/2000 | Kirkpatrick et al. |
| 6,283,877 B1 | 9/2001 | Cook |
| 6,503,086 B1 | 1/2003 | Golubov |
| 6,671,390 B1 | 12/2003 | Barbour et al. |
| 7,200,282 B2 | 4/2007 | Xu |

(Continued)

FOREIGN PATENT DOCUMENTS

| | | |
|---|---|---|
| EP | 1850321 B1 | 2/2011 |
| EP | 2280377 A1 | 2/2011 |

(Continued)

OTHER PUBLICATIONS

Chen et al., "Computer-assisted self-training system for sports exercise using Kinects", ICMEW 2013, Jul. 15-19, 2013.*

(Continued)

*Primary Examiner* — Soo Jin Park
(74) *Attorney, Agent, or Firm* — Thompson Coburn LLP

(57) ABSTRACT

Techniques where a computer or mobile device performs video analysis of a person performing a physical activity are described. The computer or mobile device performs video analysis based on one or more reference skeletons. The reference skeleton may be superimposed over captured video of the person performing the physical activity or compared to a generated player skeleton based on the captured video to determine derivation from the reference skeleton in the physical activity performed by the person.

40 Claims, 13 Drawing Sheets

Male, Age 14-16, Right Handed, 125-145 lbs, 5'6"-5'10"

(56) References Cited

U.S. PATENT DOCUMENTS

| | | | |
|---|---|---|---|
| 7,854,669 | B2 | 12/2010 | Marty et al. |
| 7,899,307 | B1 | 3/2011 | Hughes |
| 8,113,969 | B1 | 2/2012 | Martin |
| 8,162,782 | B2 | 4/2012 | Chen |
| 8,253,586 | B1 | 8/2012 | Matak |
| 8,314,840 | B1 | 11/2012 | Funk |
| 8,436,811 | B2 | 5/2013 | Lin |
| 8,626,472 | B2 * | 1/2014 | Solinsky ............... A61B 5/112 235/105 |
| 9,161,708 | B2 * | 10/2015 | Elliott .................... A63B 71/06 |
| 2002/0077200 | A1 | 6/2002 | Kreutzer |
| 2002/0183961 | A1 | 12/2002 | French et al. |
| 2002/0187860 | A1 | 12/2002 | Shoane |
| 2003/0073518 | A1 | 4/2003 | Marty et al. |
| 2005/0265580 | A1 | 12/2005 | Antonucci et al. |
| 2006/0003298 | A1 | 1/2006 | Greenshpan et al. |
| 2006/0281060 | A1 | 12/2006 | Katayama |
| 2007/0015611 | A1 | 1/2007 | Noble et al. |
| 2007/0173355 | A1 | 7/2007 | Klein |
| 2008/0182685 | A1 | 7/2008 | Marty et al. |
| 2008/0288200 | A1 | 11/2008 | Noble |
| 2008/0312010 | A1 * | 12/2008 | Marty ................ A63B 24/0003 473/447 |
| 2010/0173274 | A1 * | 7/2010 | Hutchison ............ G09B 19/003 434/258 |
| 2010/0283630 | A1 | 11/2010 | Alonso |
| 2011/0052005 | A1 | 3/2011 | Selner |
| 2011/0270135 | A1 * | 11/2011 | Dooley ................. A61B 5/1121 600/595 |
| 2011/0275045 | A1 | 11/2011 | Bhupathi et al. |
| 2011/0305369 | A1 | 12/2011 | Bentley et al. |
| 2012/0029666 | A1 | 2/2012 | Crowley et al. |
| 2012/0190505 | A1 * | 7/2012 | Shavit ................ A63B 71/0622 482/8 |
| 2012/0283049 | A1 | 11/2012 | Grover |
| 2012/0289296 | A1 | 11/2012 | Marty et al. |
| 2013/0080182 | A1 | 3/2013 | Kovach |
| 2013/0095924 | A1 * | 4/2013 | Geisner .................. A63F 13/00 463/32 |
| 2013/0102419 | A1 | 4/2013 | Jeffery et al. |
| 2013/0324368 | A1 * | 12/2013 | Aragones ............. A61B 5/6829 482/8 |
| 2013/0346009 | A1 * | 12/2013 | Winter ................... G01D 11/00 702/96 |
| 2015/0005910 | A1 * | 1/2015 | Ishii .................. G06K 9/00342 700/91 |

FOREIGN PATENT DOCUMENTS

| | | |
|---|---|---|
| WO | 2004041379 A2 | 5/2004 |
| WO | 2006103662 A2 | 10/2006 |
| WO | 2007084850 A2 | 7/2007 |
| WO | 2008010097 A2 | 1/2008 |
| WO | 2008129442 A1 | 10/2008 |
| WO | 2010085704 A1 | 7/2010 |
| WO | 2010121166 A1 | 10/2010 |
| WO | 2012146184 A1 | 11/2012 |
| WO | 2012148524 A1 | 11/2012 |
| WO | 2013002653 A1 | 1/2013 |

OTHER PUBLICATIONS

Shum et al., "Real-time posture reconstruction for Microsoft Kinect", IEEE Transactions on Cybernetics, vol. 43, issue 5, Aug. 22, 2013.*
"All About the Coach's Eye App: A Figure Skating Teaching Aid for iPhone, iPad, or iPod", About Sports, Mar. 4, 2016, http://figureskating.about.com/od/skatingtraiiningaids/p/Coachs-Eye-Figure-Skating-Teaching-Aid-For-Iphone-Ipad-Or-Ipod.htm.
"Competitive Swimmers Can Have Movements Tracked Wirelessly Through Water", Engineering and Physical Sciences Research Council, Jun. 28, 2012, http://www.sciencedaily.com/releases/2012/06/120628164440.htm.
"Stretchable Electronics: Wireless Sensor Measures and Inputs Intense Body Movements to Computer", Uppsala Universitet, Jun. 17, 2011, http://www.sciencedaily.com/releases/2011/06/110616092540.htm.
Covert, "We Could Control Future Computers and Video Games Using a 3D Motion Tracking Wristband", GIZMODO, Oct. 8, 2012, http://gizmodo.com/5949960/we-could-control-future-computers-and-video-games-using-a-3d-motion-tracking-wristband <http://gizmodo.com/5949960/we-could-control-future-computers-and-video-games-using-a-3d-motion-tracking-wristband>.
http://www.coachseye.com/.

* cited by examiner

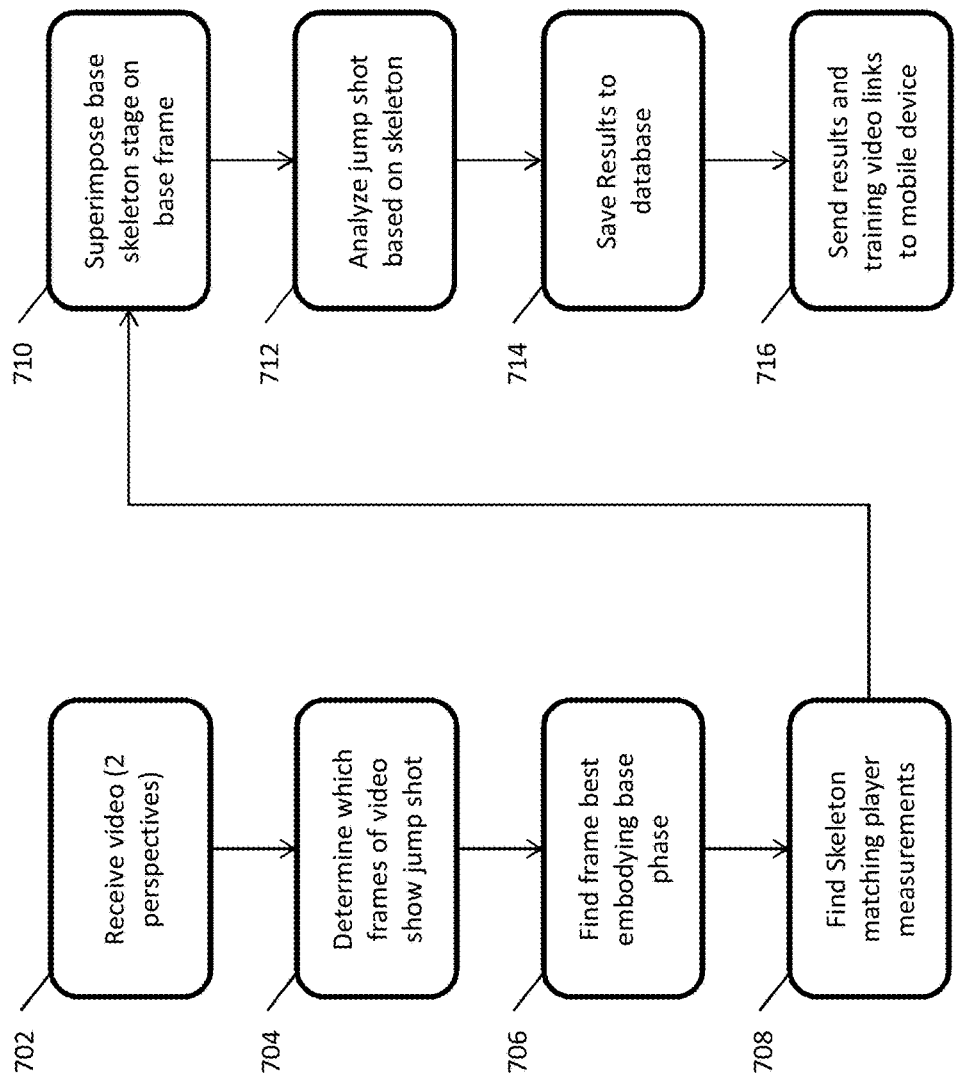

(9-B) Toes Too High Too Soon (1-B) Too Upright Not Ready (23-A) Guide Hand resists (22-A) Guide Hand shoots/thumbs (Z1-B) Low release point
430

(30-B) Land forward/stagg/twisted

Fig. 12

JUMP SHOT AND ATHLETIC ACTIVITY ANALYSIS SYSTEM

INTRODUCTION

Finely tuned fundamentals are often what separate highly skilled basketball players from less skilled basketball players. The acquisition and mastery of skills and fundamentals help players compensate for lack of height or speed on the basketball court. Skills and fundamentals should be regularly assessed and improved as a player's body and mind grows and develops. One of the most common and valued indicators of a player's basketball skills is the player's ability to shoot the basketball and score consistently. A player demonstrating a fundamentally sound jump shot generally uses proper balance, alignment, mechanics, and leverage to generate the appropriate arc angle and in-flight ball rotation that increases the likelihood of consistently scoring baskets during training and in competition over the course of the player's career.

A fundamentally sound jump shot has many important mechanics that should be regularly assessed and improved during the process of learning how to shoot a proper jump shot which has, for example, five parts from start to finish. These mechanics may include a body and base that is square to the basket, a proper knee bend and squat, a straight shooting elbow in the frame, a ball release at the pinnacle of an athlete's jump, a release that leads to optimal arc, a smooth follow through to generate in-flight ball rotation, and a consistent finishing pose. Collectively these five exemplary parts comprise a one to two second action involved in the execution of a jump shot. The mechanics that generate arc and rotation lead to softer bounces on the rim, which leads to more made baskets. Other mechanics of the fundamentally sound jump shot enhance the likelihood that the shooter directs the basketball directly at the basket. Still other mechanics decrease the likelihood of having a jump shot blocked by a defender. Having strong mechanics in a jump shot may compensate for physical limitations, such as height and arm length. Some players are gifted with the ability to jump 42 inches in the air, other players grow to be seven feet tall, but others can compensate for physical limitations with strong jump shot fundamentals.

Coaches often teach strong jump shot fundamentals to players because the proper jump shot motions are unnatural to many players. The most common conventional method for improving a jump shot remains coaching. In other words, a teacher or coach watches a player take practice jump shots, critiques the player's fundamentals, and ultimately offers corrections to improve the player's fundamentals. In other words, the human eye was used to find jump shot fundamental flaws.

Some coaches use video cameras to assist in the jump shot lessons they give to basketball players. By showing the video to a basketball player, the basketball player can see the mistakes he or she is making and hopefully quickly fix the problems. While video footage can show fundamental flaws in a basketball player's jump shot to the basketball player, the coach is still largely responsible for identifying the flaws in the jump shot technique based on his or her own visual analysis of the video. So, even though an element of technology is introduced when filming a basketball player's jump shot, the human eye is still mainly responsible for identifying mistakes in the jump shot.

Strong jump shot fundamentals are usually developed over a long time with many hours of practice. The best results are achieved when a coach insists that a player shoots perfect repetitions from a realistic and appropriate range based on the player's height, weight, and age. One-on-one coaching sessions are costly, and not every basketball player can afford frequent (e.g. daily) tutoring lessons from a coach or trainer, who often feels pressured by the paying customer to shoot out of a player's most productive range, which leads to instant gratification when one shot is made, but poor results in both the short and long term. Also, a coach only has limited time and likely has many pupils, making it difficult to properly pace and adjust one's mechanics and range over time as bodies grow and change. If a basketball player really wants to improve, he cannot practice his jump shot only when the coach is available and teaching the importance of shooting from a productive range with realistic expectations. Disciplined individual practices time devoted to mastering proper shooting mechanics from a productive and reasonable range is an absolute necessity if a player wants to become a highly skilled basketball player.

When the player participates in individual practice sessions, the player still needs feedback on whether his fundamentals are improving and whether he is following the coach's instructions. Muscle memory and "feeling" can help a player remember solid fundamentals during individual practices, but bad habits are easy to form when not under the watchful eye of a knowledgeable coach. Often, players forget the feeling they had during the training session with the coach during individual practices. Further, as a player grows or his body changes, bad habits and improper mechanics may develop. Shooting improvement requires constant checks for proper alignment, balance, and mechanics, but having the constant attention of a coach is simply not feasible for most players. Without constantly checking for improper mechanics, a player can quickly develop bad habits, which may be difficult to correct after the bad habit has been ingrained. So a method for self-checking on mechanics and fundamentals are necessary for development early on and throughout one's basketball career. Unfortunately, a consistent method for self-checking and self-regulating fundamentals is lacking in the conventional jump shot teaching methods.

Even in situations where a player has many basketball resources, such as a college player, the college team rarely provides a coach whose sole job is to teach the jump shot. College head coaches and assistant coaches are often very busy teaching players offensive plays, scouting opponents, watching game tape, or designing defensive sets, and they do not have time to teach jump shooting fundamentals. So, in just about every setting, whether a child learning to play in the backyard to a college player competing for a national championship, players need a way to learn, fine-tune, and self-regulate their jump shot.

In light of all these problems with conventional jump shot training methods, there is room for improvement in this technology area. Players need a convenient and inexpensive way to maximize their individual practices so that good fundamentals are honed during these valuable practice sessions.

It is in view of the above problems that the present invention was developed. The invention provides a system and method for analyzing captured video of a physical activity based on a reference skeleton of the physical activity on the captured video. The skeleton exhibits a fundamentally strong version of a human performing the physical activity based on a realistic and optimal expectation for a player who is of the same age, body weight, gender, or size. The skeleton may also be adapted for any skill level from a beginner to a professional basketball player. Based on the skeleton, a computer performing video analysis finds deviations from the reference skeleton performed by the person performing the physical activity.

The invention described herein provides a system that combines video analysis with working knowledge and proven results to identify and teach the physical activity for any person. The skeleton and video analysis may be altered based on age, gender, size, skill level, shooting hand, or any other variable. The skeleton may be modified for younger players who lack the strength to perform the physical activity in a way performed by grown adults and professionals. The skeleton may also be modified for skill level so that certain more basic fundamentals and mechanics are focused on by the computer performing video analysis for less skilled athletes and more refined mechanics are focused on for highly skilled athletes.

In one embodiment, a method for video analysis of a physical activity, the method comprises: processing video data, the video data comprising a plurality of frames of a person performing the physical activity, wherein the processing step comprises: determining a frame of the video data that depicts a body position of the person in a phase of the physical activity; comparing the body position in the frame with a reference skeleton for the phase of the physical activity; and determining a deviation between the frame body position and the reference skeleton based on the comparing step; and wherein the frame determining, comparing, and deviation determining steps are performed by a processor.

In another embodiment, an apparatus for video analysis of a physical activity, the apparatus comprises: a processor configured for processing video data, the video data comprising a plurality of frames of a person performing the physical activity, wherein the processor is configured to: determine a frame of the video data that depicts a body position of the person in a phase of the physical activity; compare the body position in the frame with a reference skeleton for the phase of the physical activity; and determine a deviation between the frame body position and the reference skeleton based on the comparison operation.

In another embodiment, a computer program product for video analysis of a physical activity, the computer program product comprises: a plurality of processor-executable instructions configured for processing video data, the video data comprising a plurality of frames of a person performing the physical activity, the instructions being resident on a non-transitory computer-readable storage medium and being configured, upon execution by a processor, to: determine a frame of the video data that depicts a body position of the person in a phase of the physical activity; compare the body position in the frame with a reference skeleton for the phase of the physical activity; and determine a deviation between the frame body position and the reference skeleton based on the comparison operation.

In another embodiment, a computer program product comprises: a plurality of processor-executable instructions, the instructions being resident on a non-transitory computer-readable storage medium of a computing device and being configured, upon execution by a processor, to: capture video of a person performing the physical activity using a camera associated with a mobile device; determine a first frame of the captured video that depicts the person positioned in a first phase of the physical activity by searching for characteristics identifying the first phase of the physical activity in the captured video; compare the person's body position in the first frame to a first reference skeleton corresponding to the first phase of the physical activity; and determine whether the person demonstrated a derivation from the first reference skeleton in the first phase of the physical activity while performing the physical activity as a result of comparing the first frame to the first reference skeleton.

In another embodiment, an apparatus for video analysis of a physical activity, the apparatus comprises: a processor configured for processing video data, the video data comprising a plurality of frames of a person performing the physical activity, wherein the processor is configured to: determine a frame of the video data that depicts a body position of the person in a phase of the physical activity; compare the body position in the frame with a reference skeleton for the phase of the physical activity; determine a deviation between the frame body position and the reference skeleton based on the comparison operation; determine whether the basketball jump shot went through a basketball hoop; a database for storing data, the database configured to: maintain data indicative of whether the basketball jump shot went through a basketball hoop; and maintain data indicative of one or more determined derivations between the frame body position and the reference skeleton.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 7 illustrates a flow chart of a remote server performing video analysis of the jump shot according to an exemplary embodiment.

FIG. 12 illustrates an exemplary result spreadsheet displayed to a user after video analysis.

DETAILED DESCRIPTION

Figure 1:
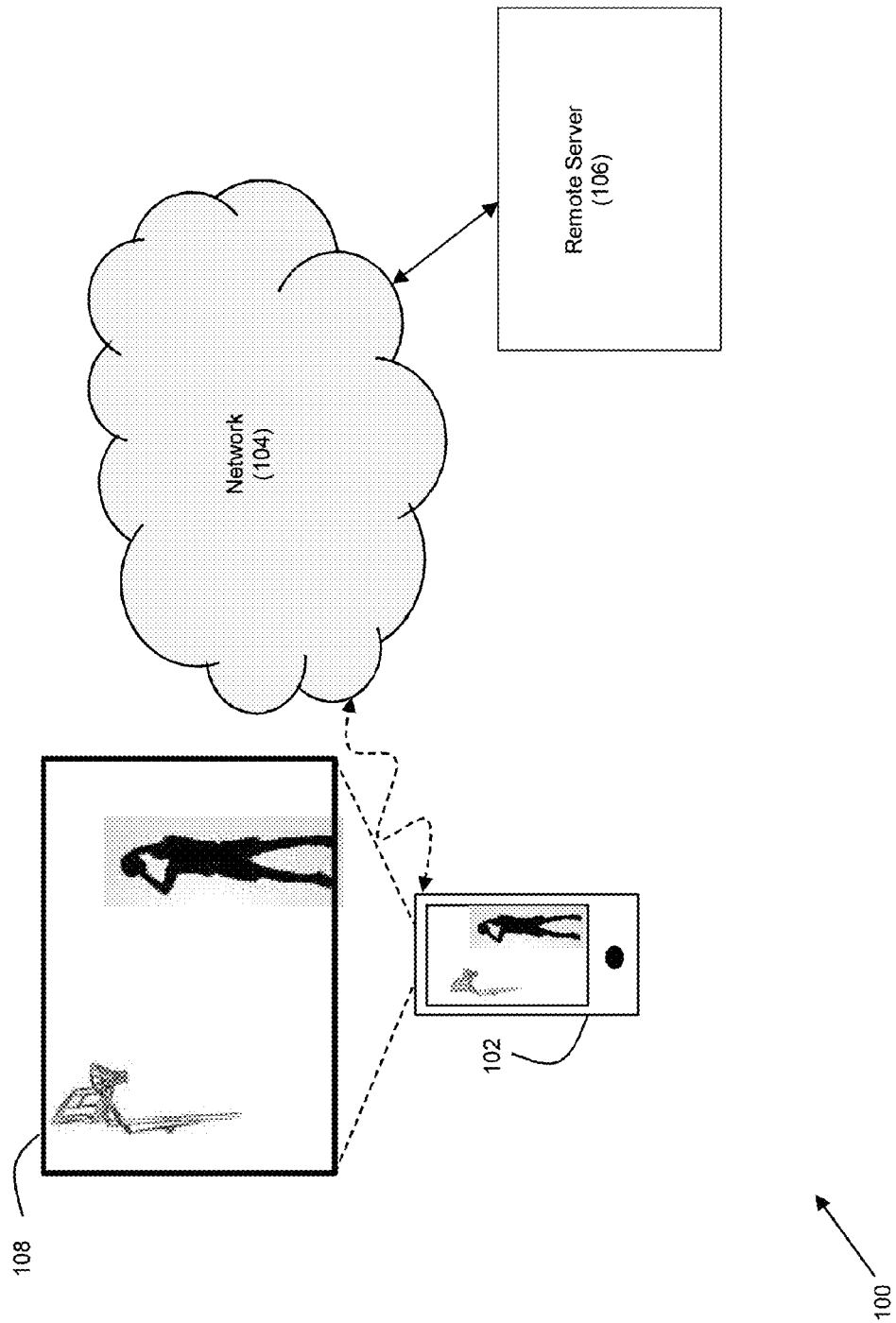
FIG. 1 illustrates an exemplary system that employs a mobile device to capture video of a physical activity.

Referring to the accompanying drawings in which like reference numbers indicate like elements, FIG. 1 illustrates an exemplary system 100 for an embodiment that employs a mobile device to capture videos of a player taking a jump shot 108. The system 100 may comprise at least one mobile device 102 in communication with a remote server 106 via a data communications network 104. In one embodiment, the remote server 106 receives videos taken by the mobile device 102 of the player's jump shot 108 and performs video analysis on the videos. Based on a reference jump shot skeleton, the remote server 106 may determine deviations from the reference skeleton in the player's jump shot 108. While FIG. 1 has been illustrated to include a remote server 106 performing video analysis, the mobile device 102 may perform video analysis. In another embodiment, the mobile device 102 may connect to a remote server 106 even though the mobile device 102 performs video analysis. In this embodiment, the remote server 106 may be a web server where basketball players may upload their results, receive training schedules, games, and tutorials, or share their training results with social media connections. The remote server 106 may be configured to track a player's progress as they train using the system 100. As will be seen by the exemplary embodiments described below, the remote server 106 may provide numerous functions to help players improve.

The mobile device 102 may be a smart phone (e.g., an iPhone, a Google Android device, a BlackBerry device, etc.), tablet computer (e.g., an iPad), a laptop computer (e.g. MacBook) or the like. Furthermore, the mobile device 102 may be a position tracking-enabled mobile device. That is, the mobile device 102 may be configured to track its geographic position and communicate data regarding same to other computing devices (e.g., the remote server 106). The mobile device preferably employs a touchscreen or the like for interacting with a user. However, it should be understood that any of a variety of data display techniques and data input techniques could be employed by the mobile device. For example, to receive inputs from a user, the mobile device need not necessarily employ a touchscreen—it could also or alternatively employ a keyboard or other mechanisms. The mobile device 102 also comprises a video camera for capturing photos and videos of the player's jump shot 108.

Figure 2B:
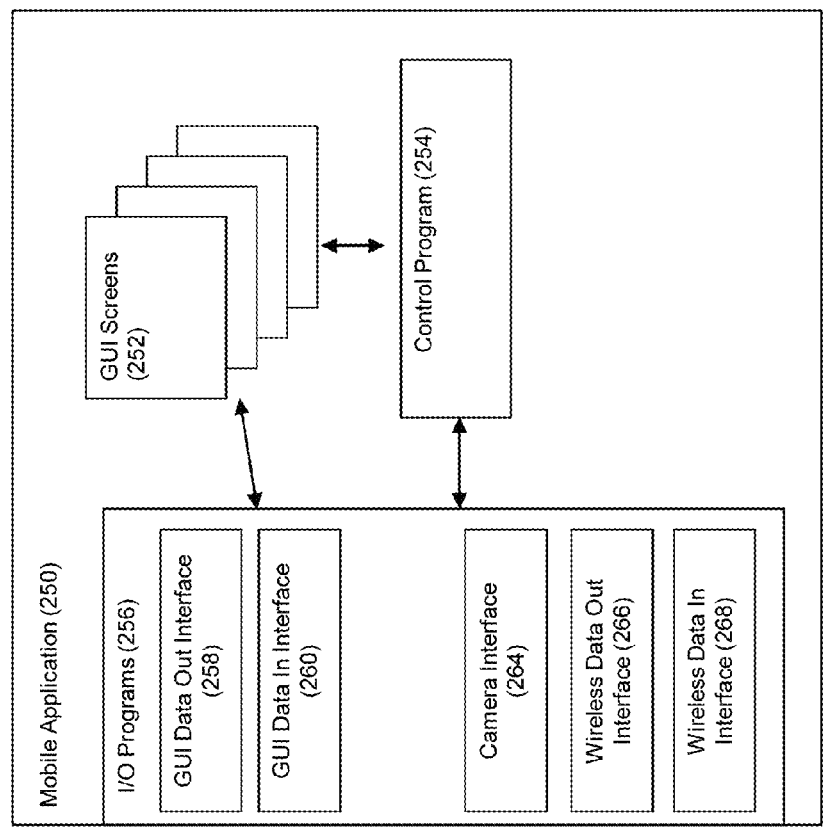
FIG. 2(b) illustrates an exemplary architecture for a mobile application executed by a mobile device.
Figure 2A:
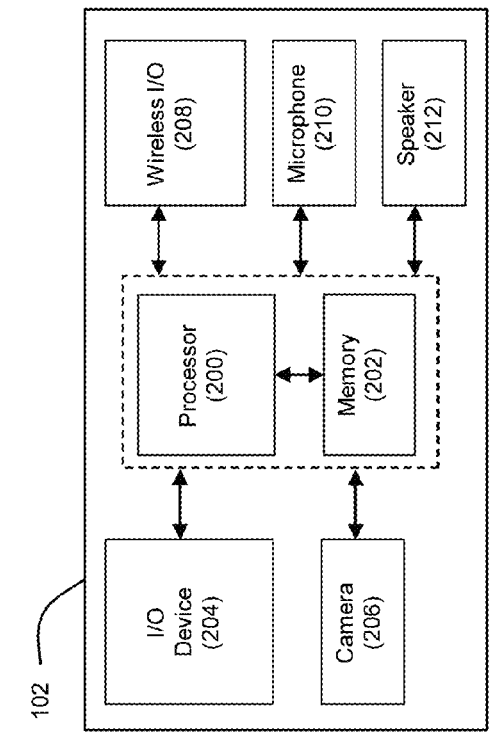
FIG. 2(a) illustrates an exemplary embodiment for a mobile device.

FIG. 2(a) depicts an exemplary embodiment for a mobile device 102. The mobile device 102 may comprise a processor 200 and associated memory 202, where the processor 200 and memory 202 are configured to cooperate to execute software and/or firmware that support operation of the mobile device 102. Furthermore, the mobile device 102 may include an I/O device 204 (e.g., a touchscreen user interface for graphically displaying output data and receiving input data from a user), a camera 206, wireless I/O 208 for sending and receiving data, a microphone 210 for sensing sound and converting the sensed sound into an electrical signal for processing by the mobile device 102, and a speaker 212 for converting sound data into audible sound. The wireless I/O 208 may include capabilities for making and taking telephone calls, communicating with nearby objects via near field communication (NFC), communicating with nearby objects via RF, and/or communicating with nearby objects via Bluetooth. These components are now resident in many standard models of smart phones and other mobile devices.

FIG. 2(b) depicts an exemplary mobile application 250 for an exemplary embodiment. Mobile application 250 may be installed on the mobile device 102 for execution by processor 200. The mobile application 250 preferably comprises a plurality of computer-executable instructions resident on a non-transitory computer-readable storage medium such as a computer memory. The instructions may include instructions defining a plurality of GUI screens for presentation to the user through the I/O device 204. The instructions may also include instructions defining various I/O programs 256 such as:
- a GUI data out interface 258 for interfacing with the I/O device 204 to present one or more GUI screens 252 to the user;
- a GUI data in interface 260 for interfacing with the I/O device 204 to receive user input data therefrom;
- a camera interface 264 for interfacing with the camera 206 to communicate instructions to the camera 206 for capturing an image in response to user input and to receive image data corresponding to a captured image from the camera 206;
- a wireless data out interface 266 for interfacing with the wireless I/O 208 to provide the wireless I/O with data for communication over the network 104; and
- a wireless data in interface 268 for interfacing with the wireless I/O 208 to receive data communicated over the network 104 to the portable computing device for processing by the mobile application 250.

The instructions may further include instructions defining a control program 254. The control program may be configured to provide the primary intelligence for the mobile application 250, including orchestrating the data outgoing to and incoming from the I/O programs 256 (e.g., determining which GUI screens 252 are to be presented to the user).

The network 104 may be any data communications network capable of supporting communications between the remote server 106 and the mobile device 102, wherein at least a portion of the data communication is wireless data communication as shown in FIG. 1. It should be understood that network 104 may comprise multiple data communication networks that interconnect to form a larger network. The network 104 may be public, private, or a mix of public and private networks.

The remote server 106 may be a server or collection of servers that are configured to support video processing as described herein. The remote server 106 may perform other activities other than or in addition to video analysis, such as tracking improvements in a player's jump shot 108, storing tutorial and training videos, storing training games, generating a training schedule including training activities to be performed on each day, sharing training results via social media, storing all the videos taken of the player's jump shot 108, connecting with coaches, providing a community where a player may upload questions about training, or any other web-based service to help a player improve their training and jump shot 108. The remote server 106 may be operated by sports training company. However, it should be understood that other entities may operate the system.

Figure 3:
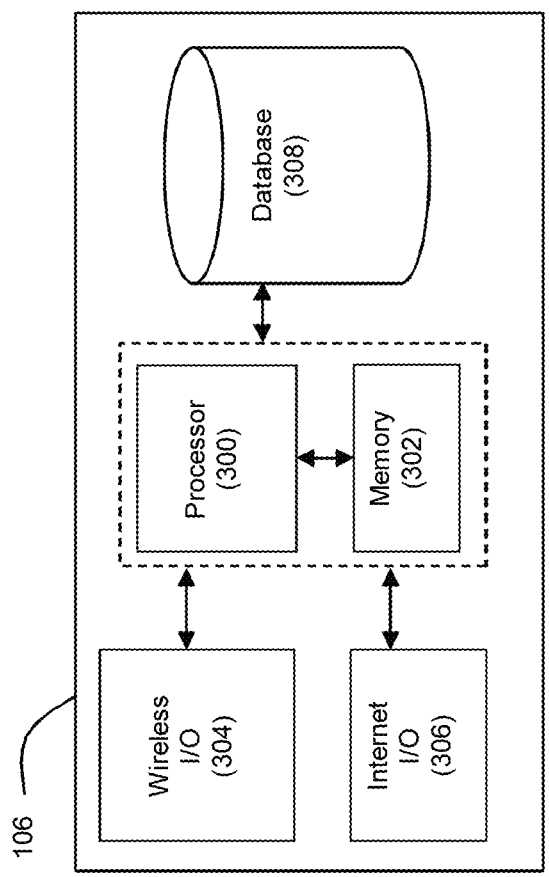
FIG. 3 illustrates an exemplary embodiment for a remote server.

FIG. 3 depicts an exemplary embodiment of the remote server 106. The remote server 106 may comprise a processor 300 and associated memory 302, where the processor 300 and memory 302 are configured to cooperate to execute software that performs transaction processing as described herein. A memory in the form of a database 308 may be configured to store various data structures representative of jump shot videos, jump shot training schedules, tutorial videos, and previous jump shot video analysis results. The system 106 may further comprise one or more I/O interfaces (e.g., I/O interfaces 304 and 306 for communicating via wireless RF and Internet links, respectively). It should be understood that FIG. 3 is exemplary only, and a practitioner may distribute the processing tasks described herein among numerous processors as well as distribute the data storage tasks described herein among numerous databases.

While basketball has been and will be the focus of the disclosure, the video analysis features taught by the present disclosure can be applied to any sport or physical activity.

Either the mobile device 102 processor 200 or the remote server 106 processor 300 performs video analysis of a player's jump shot 108 based on an reference jump shot skeleton. If the remote server 106 performs video analysis, the mobile device 102 transmits the video files of the jump shot to the remote server 106. If the mobile device 102 performs video analysis, the mobile device may still communicate with the remote server 106 by requesting the remote server to store training results, training videos, or other data, in the database 308.

Figure 4:
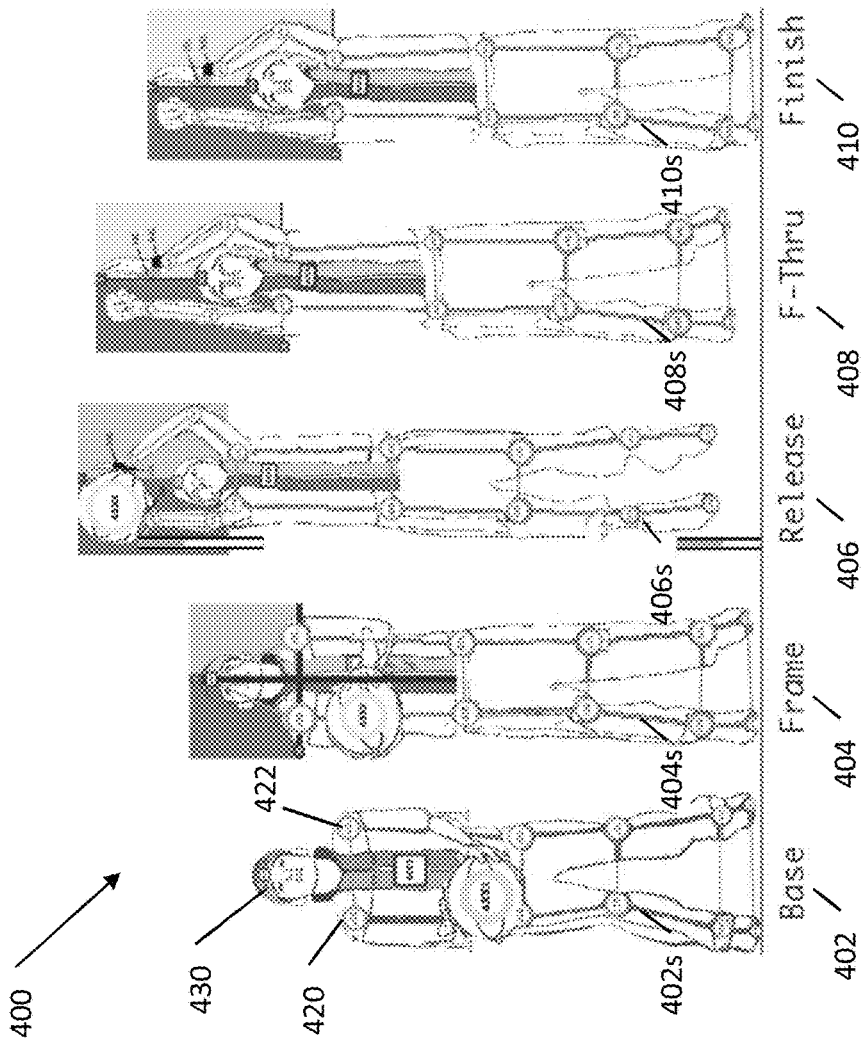
FIG. 4 illustrates a reference skeleton of a basketball jump shot from a front perspective according to an exemplary embodiment.
Figure 5:
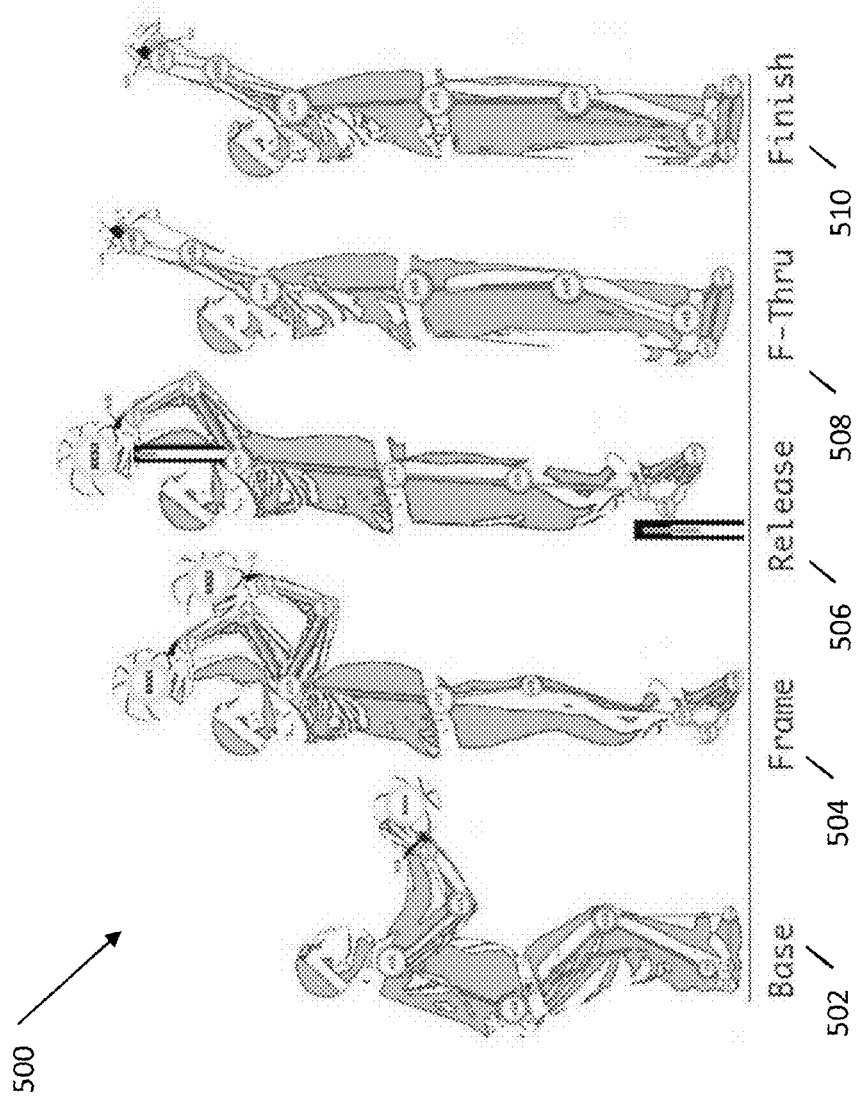
FIG. 5 illustrates the reference skeleton of a basketball jump shot from a side perspective according to an exemplary embodiment.

FIGS. 4 and 5 illustrate a front view reference jump shot skeleton 400 and a side view reference jump shot skeleton 500. A jump shot has multiple components or phases as a player jumps in the air and releases the basketball. The exemplary embodiments disclosed herein have determined that five phases represent the most important aspects of a jump shot, but the jump shot may have more intermediate phases. These phases include: a base phase 402, 502, a frame phase 404, 504, a release phase 406, 506, a follow-through phase 408, 508, and a finish phase 410, 510. The reference jump shot skeletons 400, 500 may be a collection of images each representing a phase of the jump shot. So, just as the jump shot may have five phases, the reference jump shot skeleton 400, 500 may have five or more images matching the five phases of the jump shot. Alternatively, the reference jump shot skeletons 400, 500 may be data points derived from an image.

FIG. 4 illustrates the reference jump shot skeleton 400 from a front view, or a view where the player is facing the camera 206. FIG. 5 illustrates the reference jump shot skeleton 500 from a side view, or a view where the camera captures the jump shot from the right or left side of the player. In the examples shown in FIGS. 4 and 5, a skeleton for a male age 14-16 is illustrated. The player 430 illustrated in FIGS. 4 and 5 may be right-handed, weighs approximately 125-145 pounds, and may have a height of about 5'6"-5'10".

The skeleton 400, 500 illustrated in FIGS. 4 and 5 illustrates a mid-air jump shot, where the player releases the ball at the pinnacle of their jump. Not all people can perform a mid-air jump shot, such as younger players or some female players. For example, a younger player who has not fully grown may demonstrate more of a "push" shot (set shot), wherein the player uses the arm motion and leg jump to help push the ball at the basket. This pushing mechanic occurs because younger players are not strong enough to shoot the ball at a ten foot rim with simply a wrist flick and arm extension. Other players are strong enough to perform a mid-air jump shot, but still need to perform some pushing action for longer jump shots (e.g. shots taken behind the three-point line). The jump shot with some pushing action may be called a modified jump shot. A skeleton 400, 500 may be altered to analyze a modified jump shot, a set shot, or a mid-air jump shot upon user command. The skeleton 400, 500 may be changed for gender, age, height, weight, shooting hand, and skill level. For example, a skeleton for a 8-10 year old may accommodate a set shot so that the younger player can focus on other mechanics such as alignment, balance, and footwork, which are things the younger player can control while he is still growing. For example, the skeleton age ranges may include a skeleton for age ranges of 9-11 year, 12-13 years, 14-16 years, and 17+ years. In this way, the skeleton 400, 500 grows with the player. The skeleton 400, 500 is not just a "one-size fits all" model. The skeleton 400, 500 accounts for player's physical limitations, basketball skill, and body size.

The side view angle may capture ball flight and also whether the ball went through the hoop. The front view skeleton 400 may have the same number of phases as the side view skeleton 500, but the front view skeleton 400 is different than the side view skeleton 500 because of the camera's 206 perspective. FIGS. 4 and 5 show the skeletons 400, 500 superimposed over an a basketball player. The skeletons 400, 500 are generated by analyzing strong shooters, gathering data about joint locations for the strong shooters, body positions for the strong shooters, calculating a standard deviation across all analyzed shooters, and ultimately generating a reference skeleton 400, 500. The computer performing video analysis (either the mobile device 102 or the remote server 106) may generate different skeletons 400, 500 based on age, race, gender, height, weight, etc of a player 430. A plurality of skeletons 400, 500 may be saved in a database 308 and applied based on data inputted by a user of the mobile device 102 about the player 430. Or, the database 308 may store very few skeletons 400, 500 and stretch the dimensions of generic skeletons 400, 500 based on the player's 430 body measurements.

The reference jump shot skeleton 400, 500 may comprise joints and connecting lines between the joints. The reference jump shot skeletons 400, 500 should roughly resemble a human body taking a jump shot, and the joints of the reference jump shot skeletons 400, 500 should generally overlap the joints of the player being filmed. Referring to FIG. 4, the shoulder joints 420, 422 correspond to the player's 430 shoulders. The same is true for the player's 430 knees, hips, elbows, or even the basketball itself. Matching skeleton 400, 500 joints with joints found on the player in the video taken of the player's 430 jump shot 108 may be performed while analyzing the player's 430 jump shot 108. By matching skeleton 400, 500 joints with joints on the basketball player 430, the connecting lines match the player's body, limbs, head, etc. If a player joints do not closely overlap with the reference skeleton 400, 500 when the skeleton 400, 500 is superimposed on a video of the player's 430 jumps shot, deviations from the skeleton 400, 500 may be determined by the remote server 106 or the mobile device 102.

In another embodiment, the computer performing video analysis 102 or 106 may analyze a frame of video and find joints, limbs, or body positions of the player 430. The computer performing video analysis 102 or 106 may determine joint locations and body positions by determining the edges of a player's body and the size of the player's body. The computer performing video analysis 102 or 106 may quantify the size of the player 430 and also define coordinates for certain edges of the player 430 in the video. Based on the size and edge coordinates, the computer performing video analysis 102 or 106 may determine joint coordinates in the image. Coordinates may be pixel locations, generated X-Y plane values, or any other generated image coordinate system. The computer performing video analysis 102 or 106 has a basic understanding of the shape of a human and may determine shoulder joints from elbow joints using the edge coordinates and the general shape understanding. For example, if a first edge coordinate is located relatively closely to a second edge coordinate along the X-axis, the computer may determine an arm or a leg. The computer may scan a number of lines along the X-axis searching for known areas of the body. After finding the joints and limbs, the computer performing video analysis 102 or 106 may generate a player skeleton that actually represents the player's body positions in the video. The player skeleton may be compared to the reference skeleton on an X-Y plane to find deviations from the skeleton 400, 500. In places where joints or connecting lines of the reference skeleton 400, 500 substantially deviate from the player skeleton, the computer performing video analysis 102 or 106 may determine deviations from the skeleton 400, 500 in the jump shot. The computer performing video analysis 102 or 106 may choose either method of video analysis.

The skeleton 400, 500 has a finite number of stages. FIGS. 4 and 5 show that the skeleton 400, 500 has five stages, matching the five above-described phases of the jump shot. The skeleton 400, 500 may have more or less than five stages, but if the skeleton 400, 500 has many more stages the amount of video analysis performed by a computer substantially increases. A substantial amount of video analysis becomes a problem for processors with lower performance specifications, such as the processor 200 in the mobile device 102. So a balance needs to be found between the number of video frames analyzed and the amount of processing power possessed by the processor performing video analysis.

Basketball players differ in height, weight, and gender, so the skeleton 400, 500 may stretch or constrict based on a player's size. In order to account for a basketball player's size, a user of the mobile device 102 may input size measurements before capturing video so that the computer performing video analysis 102 or 106 may generate a skeleton roughly matching the basketball player's 430 size. These body measurements may be general or specific. For example, a general body measurement may include the basketball player's 430 height, weight, and gender. Based on the height, weight, and gender, the computer performing video analysis 102 or 106 may generate a skeleton that roughly matches what an average person having those height and weight attributes should look like. For example, if a player is very tall, the computer performing video analysis 102 or 106 may stretch the connecting lines between joints representing the legs, arms, and torso. As another example, a male skeleton may have a slightly longer torso than a female skeleton because females generally have a lower center of gravity. Alternatively, a user could input more specific body measurements, such as height, weight, arm length, shoulder width, leg length, etc. The application 250 may request even more specific attributes, like forearm length, a measurement from knee to ankle, foot size, or the like. Basketball players tend to be lanky, so arm length and leg length may greatly vary from player to player. If the computer performing video analysis 102 or 106 receives very accurate and specific measurements, the computer performing video analysis 102 or 106 may generate a very accurate skeleton 400, 500 and determine jump shot deviations from the skeleton 400, 500 very accurately.

The computer performing video analysis 102 or 106 may further be able to stretch or shrink the skeleton 400, 500 based on the distance between the player 430 and the camera 206. The player 430 may appear smaller or larger depending on the distance between the camera 206 and the player 430. The computer performing video analysis 102 or 106 may account for camera distance by stretching or constricting the skeleton 400, 500. The application 250 may also notify a user of a suggested distance between the camera 206 and the player 430 for the video footage from each angle.

The computer performing video analysis 102 or 106 may receive multiple videos from a front perspective and a side perspective. The video taken from the side perspective allows the video performing video analysis 102 or 106 to determine the arc of the jump shot, determine whether the ball went through the hoop, and perform analysis of the player's 430 mechanics from the side based on the side perspective skeleton 500. For example, the computer performing video analysis 102 or 106 may determine if a player 430 is jumping forward a significant amount. Ideally, the location where the player 430 left the ground and the location where the player 430 lands should be substantially similar. If the player 430 jumped forward a significant amount or leaned forward while shooting, the computer performing video analysis 102 or 106 may detect such mechanical flaws using video taken from the side perspective.

Receiving high quality video greatly reduces errors in video analysis. Typically good video analysis footage includes a high resolution, good lighting, camera stability, and a consistent background. For example, if the background is substantially the same color, the computer performing video analysis 102 or 106 may determine the subject of the analysis quickly and with less processing power. The application 250 may offer video capturing tips before the application 250 begins capturing video of the jump shot 108, such as tips for holding the camera still, tips for a preferred background, and an idea distance from the shooter. Further, the application 250 may check the video footage quality before performing video analysis or sending the video to the remote server 106 for video analysis. If the application 250 determines that the video quality is poor, the application 250 may alert the user that another video should be taken of the player's 430 jump shot 108.

When a video is taken of the player's 430 jump shot 108, the mobile device's 102 camera 206 captures a plurality still frames, which when played in a sequence appear to the human eye as a moving picture. The mobile device 102 camera 206 captures approximately 24-30 frames per second. So, depending on how long the camera 206 captures video, the computer performing video analysis 102 or 106 determines which frames match the various skeleton 400, 500 stages. The computer performing video analysis 102 or 106 may need to only analyze one video frame per skeleton 400, 500 stage. So, if the skeleton comprises five stages, the computer performing video analysis 102 or 106 may search for five video frames that match the five skeleton 400, 500 stages. For example, the base stage 402, 502 has low ball position and slightly bent knees. So, the computer performing video analysis may determine which video frame depicts the player 430 with bent knees and a low ball position. Given the characteristics of the base phase 402, 502, the computer performing video analysis 102 or 106 may determine which frame captured the player 430 with the most knee bent by finding, for example, the frame where the player's head is lowest in the frame. A frame determined to be the frame embodying the base phase 402, 502 may be analyzed, for example, by superimposing the base stage 402, 502 image of the skeleton 400, 500. Because each phase of the jump shot has identifying characteristics, the computer performing video analysis 102 or 106 may use the identifying characteristics to find a frame that matches each phase of the jump shot. For example, the computer performing video analysis 102 or 106 may find a frame where the player 430 is on his toes but not quite in the air for the frame phase 404, 504, a frame where the player 430 is at the crest of his jump for the release phase 406, 506, a frame where the ball has left the player's hand for the follow through phase 408, 508, and a frame where the player has landed again for the finish phase 410, 510.

The computer performing video analysis 102 or 106 finds a video frame for each jump shot phase from both the front perspective and the side perspective. In this way, the computer performing video analysis 102 or 106 finds a frame from the front perspective for each jump shot phase and a frame from the side perspective for each jump shot phase. Subsequently, each skeleton stage from the front skeleton 400 is superimposed on a corresponding frame captured from the front perspective, and each skeleton stage from the side skeleton is superimposed on a corresponding frame captured from the side perspective.

It is important that the computer performing video analysis 102 or 106 determine the base phase 402, 502 first because then the computer 102 or 106 may ignore any frames occurring before the determined base phase 402, 502 when searching for the subsequent phases of the jump shot.

Based on the number of frames between the frame determined to be the base phase 402, 502 and the frame determined to be the follow through phase 408, 508, the computer performing video analysis may determine how quickly the player is releasing the ball. A quick release is very important in basketball because it gives a defender less time to react to a jump shot, thereby decreasing the likelihood of a blocked shot or the defender blocking the player's 430 view of the basket. So, the computer performing video analysis 102 or 106 may suggest drills and fundamental tweaks for a quicker release if the computer performing video analysis 102 or 106 determines that the release is happening too slowly.

Further still, the computer performing video analysis 102 or 106 may determine whether the ball was released at the pinnacle of the player's 430 jump by determining which video frame displays the player at the highest jump point. The computer performing video analysis 102 or 106 may determine where the ball is located within the frame determined to be the highest jump point to determine whether the player released the ball at the pinnacle of the jump shot. The computer performing video analysis 102 or 106 may analyze body control during all phases of the jump shot. For example, the computer performing video analysis 102 or 106 may analyze a player's balance and body position while stepping into the jump shot, or the computer performing video analysis 102 or 106 may analyze whether the player jumped and landed at substantially the same location on the floor. If body control issues are found, the computer performing video analysis 102 or 106 may suggest that the player moves closer to the basket knowing it is easier to master mechanics from a closer, achievable range without jumping forward. The computer performing video analysis 102 or 106 may also suggest drills and critiques to improve the player's body control during the jump shot. For example, having a proper knee bend and squat may help the player control his body during the jump and increase the player's range over time.

The computer performing video analysis 102 or 106 may also track the arc angle of the shot taken. Using the side angle video, the computer performing video analysis 102 or 106 may find the ball and track the ball's position at various points in the ball flight to calculate an arc angle. For example, the optimal arc angle may be between 45 and 60 degrees. The arc angle may be calculated on the ascent when the ball leaves the player's 430 hand and during the decent as the ball travels toward the basket. Based on the calculated arc angle, the computer performing video analysis 102 or 106 may suggest critiques, games, or training videos to help a player improve their jump shot arc angle.

As described above, the computer performing video analysis 102 or 106 may superimpose one of the skeleton 400 or 500 stages onto a frame determined to correspond with the stage. For example, the computer performing video analysis 102 or 106 determines a frame that best matches the base phase 402 and superimposes a base skeleton stage 402s onto the frame. The computer performing video analysis 102 or 106 compares the skeleton's 402s joint and connector locations and the player's 430 joint, limb, and body positions. Alternatively, the computer performing video analysis 102 or 106 may generate the player skeleton and then compare the player skeleton to the reference skeleton 400, 500. Based on the comparisons, the computer performing video analysis 102 or 106 determines deviations from the skeleton 400, 500 in the jump shot, if any.

For example, if the player 430 performs very little knee bend and squat in the base phase 402, 502, the knees and hip joints for the skeleton 400, 500 are going to be lower than the player' 430 knees and hip locations. After determining that the skeleton's 400, 500 knees and hip joint are lower than the player's 430 knees and hips, the computer performing video analysis 102 or 106 may find the deviations from the skeleton 400, 500 in the player's base phase 402, 502, more specifically, in their knee bend and squat. A deeper knee bend and squat may produce more upward thrust when leaping, which helps send the ball toward the basket.

Figure 8B:
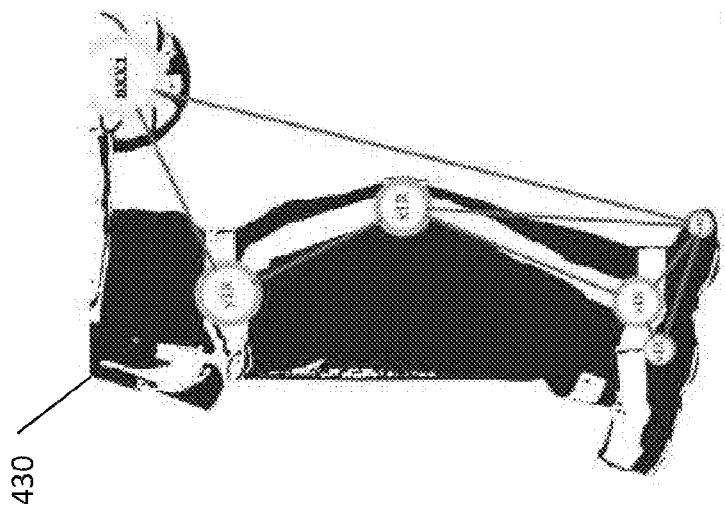
FIGS. 8(a) and 8(b) illustrate deviations from a reference skeleton in a base stage of the jump shot.
Figure 8A:
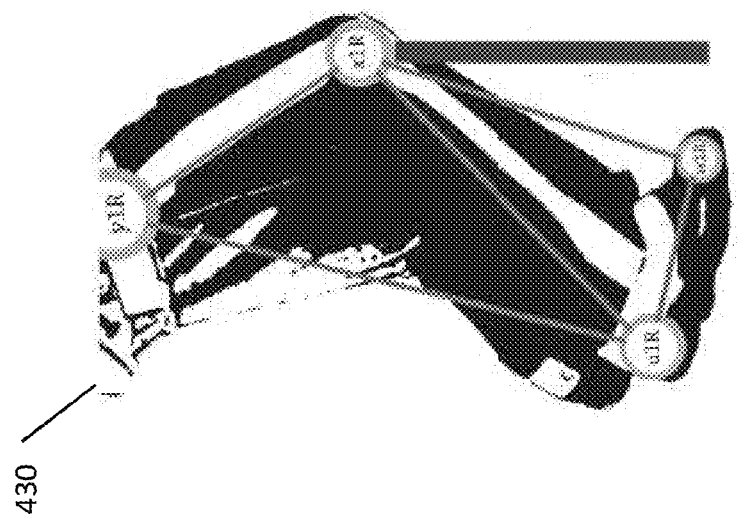

For example, FIGS. 8(a) and 8(b) illustrates two common problems the computer performing video analysis 102 or 106 may determine in the base phase 402, 502. As shown in FIG. 8(a), the player 430 is too upright, without enough knee bend and squat. As shown in FIG. 8(b), the player 430 is not balance on his feet, and his toes are off the floor to early.

The computer performing video analysis 102 or 106 performs same frame determination and skeleton 400, 500 comparison processes for all phases of the jump shot from both the front perspective and the side perspective.

Figure 9B:
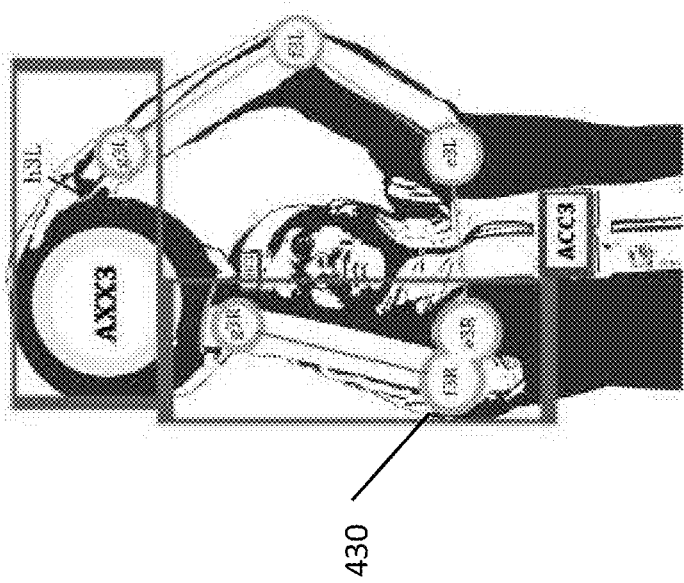
FIGS. 9(a) and 9(b) illustrate deviations from a reference skeleton in a frame stage of the jump shot.
Figure 9A:
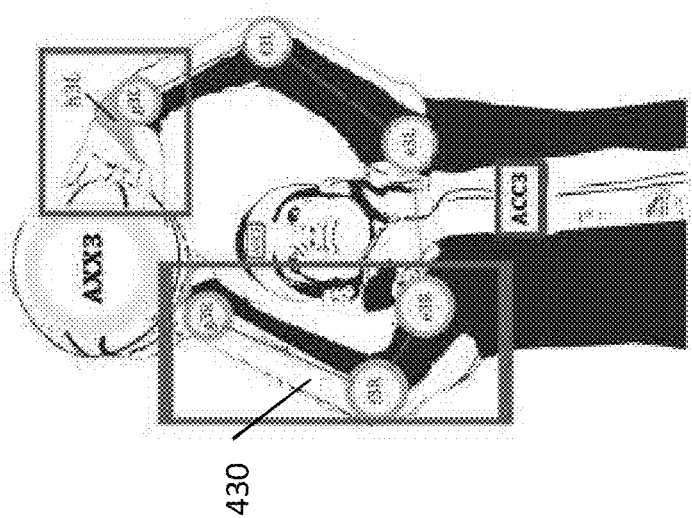

For example, FIGS. 9(a) and 9(b) illustrate two deviations from the skeleton 400, 500 in the frame phase 404, 504. As shown in FIG. 9(a), the player's 430 elbow flares out away from his body during the frame phase 404, 504. As shown in FIG. 9(b), the player's 430 misplaces his guide hand and is adding resistance against the player's 430 shooting hand.

Figure 10:
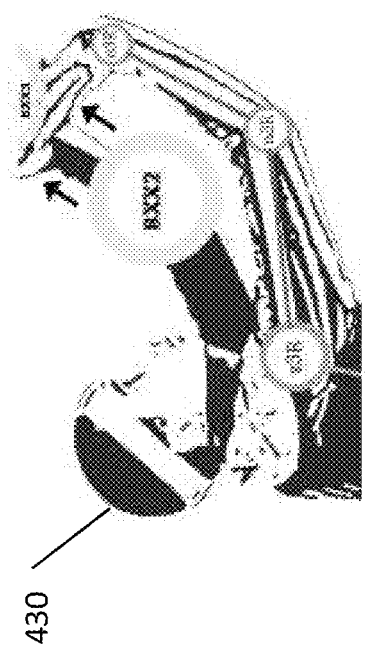
FIG. 10 illustrates a deviations from a reference skeleton in a release stage of the jump shot.

As another example, FIG. 10 illustrates a deviation from the skeleton 400, 500 in the release phase 406, 506. As shown in FIG. 10, the player's 430 release point is too low, which may lead to a poor ball flight arc.

Figure 11B:
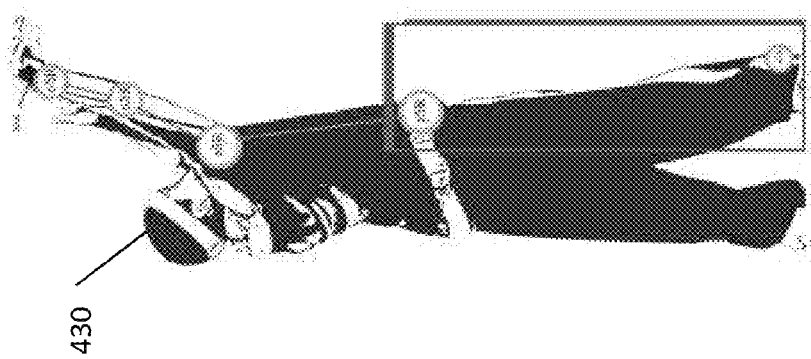
FIGS. 11(a) and 11(b) illustrate deviations from a reference skeleton in a finish stage of the jump shot.
Figure 11A:
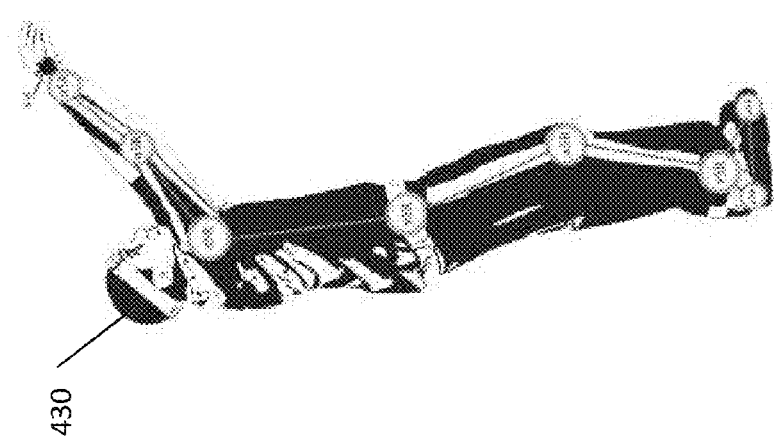

FIGS. 11(a) and 11(b) illustrate two deviations from the skeleton 400, 500 in the finish phase 410, 510. As shown in FIG. 11(a), the player 430 is falling backwards showing that the player 430 was not balanced throughout the entire jump shot. As shown in FIG. 11(b), the player's 430 legs are twisted, again showing a lack of balance and that the player 430 was not square to the basket.

FIGS. 8-11 show only a few of the many possible deviations from the skeleton 400, 500 that the computer performing video analysis 102 or 106 may find when analyzing the video frames captured by the mobile device 102. Also, FIGS. 8-11 illustrate the embodiment where the computer performing video analysis generates a player skeleton before comparing the jump shot to the reference skeleton 400, 500. When comparing these generated skeletons to the reference skeletons 400, 500 shown in FIGS. 4-5, the problems in the jump shot may be determined by the computer performing video analysis 102 or 106.

Figure 6:
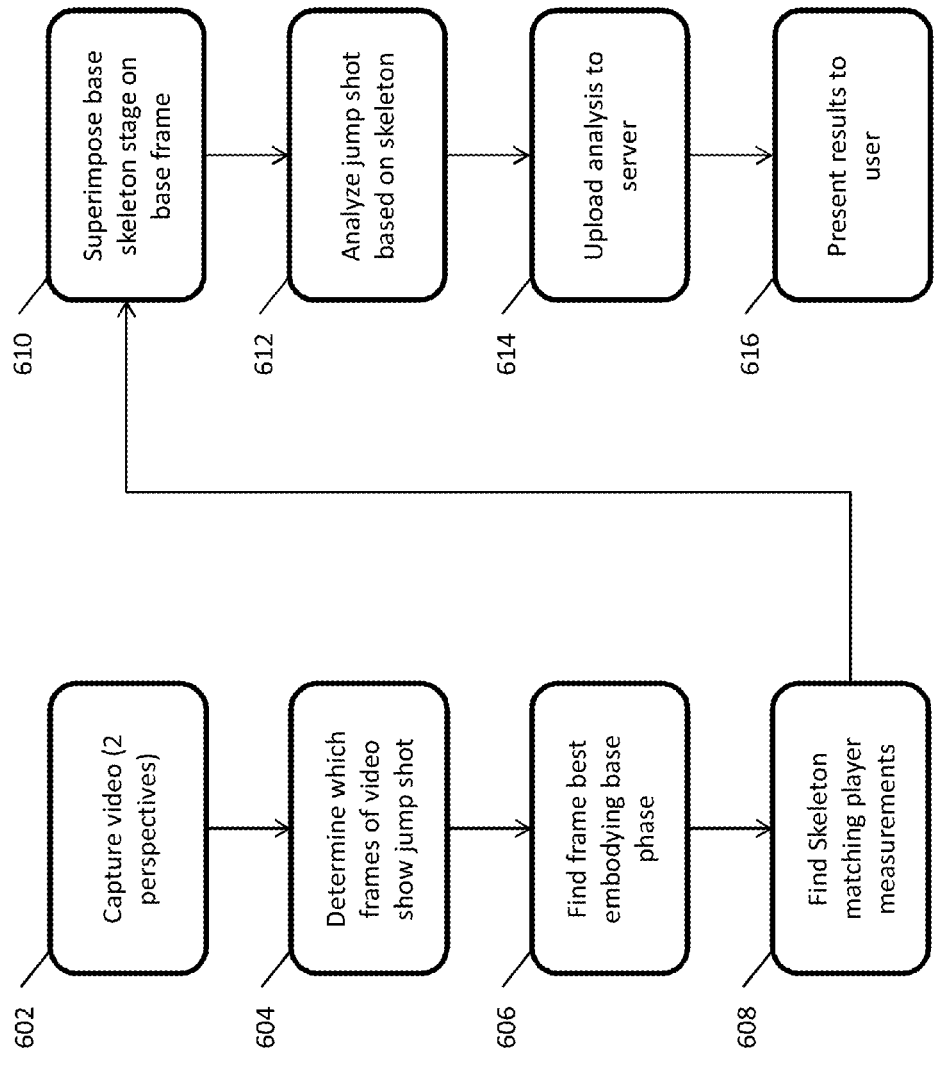
FIG. 6 illustrates a flow chart of a mobile device performing video analysis of the jump shot according to an exemplary embodiment.

After deviations from the skeleton 400, 500 are determined, the computer performing video analysis 102 or 106 may detect a player's skill level. The computer performing video analysis 102 or 106 may determine the player's skill level based on the number of determined deviations between the reference skeleton 400, 500 and the player's body movements. If the player is a beginner, the computer performing video analysis 102 or 106 may report only the most basic, major deviations from the skeleton 400, 500 to the player so that the player may build a solid foundation. For example, if a beginner player does not have his feet and shoulders square in the base phase 402, 502, the computer performing video analysis 102 or 106 may recommend drills and critiques to fix this basic deviation from the skeleton 400, 500. After basic deviations from the skeleton 400, 500 are fixed, the computer 102 or 106 may suggest further refinements for more advanced players. Meanwhile, the computer performing video analysis 102 or 106 may report more minor deviations from the skeleton 400, 500 to a more advanced player. For example, if an advanced player has a square body to the basket and a strong follow through, the computer performing video analysis 102 or 106 may recommend drills and methods to take quicker shots or increase ball rotation. The computer may track the player's 430 progress FIG. 6 illustrates a method 600 for video analysis, whereby the mobile device 102 performs video analysis. The method 600 begins in step 602 when the mobile device 102 captures video of the player 430 taking a jump shot. The mobile device 102 captures the player 430 taking jump shot from at least two perspectives. Preferably, these perspectives are a front perspective and a side perspective. Also, preferably, the mobile device 102 is held very still and captures high quality video footage against a still background.

Subsequently, in step 604, the mobile device 102 determines which frames of the video footage captured by the mobile device 102 camera 206 actually represent the player 430 taking a jump shot. Any video frames not representing the jump shot, such as frames where the player is dribbling, are disregarded. Only frames where the player 430 is taking a jump shot are analyzed. As a result, only about one-three seconds of footage needs to be analyzed for jump shot fundamentals. This determining step is performed on both the front perspective footage and the side perspective footage.

After disregarding extra footage, the processor 200 of the mobile device 102 searches the frames depicting the jump shot for a frame best representing the base phase 402, 502 in step 606. For example, the processor 200 finds the frame where the player is lowest in his squat to find the frame representing the base phase 402, 502 of the jump shot. This searching step is performed on both the front perspective footage and the side perspective footage.

After finding the frame depicting the base phase, the processor 200 generates a skeleton 400, that matches the player's 430 measurements in step 608. The method 600 assumes that a user has already inputted player 430 measurements (height, weight, arm length, gender, etc.) into to the mobile device 102. If not, the application 250 may prompt the user to enter such information before generating the skeleton 400, 500. The processor 200 references the front perspective skeleton 400 matching the player's measurements and the side perspective skeleton 500 matching the player's measurements.

In step 610, the processor 200 superimposes the base stage 402, 502 skeleton 400, 500 onto the frame determined to depict the base phase 402, 502 of the jump shot. This superimposing step is performed on both the front perspective frame and the side perspective frame.

Next, the processor 200 analyzes the player's 430 base phase 402, 502 fundamentals based on the superimposed skeleton 400, 500 in step 612. Depending on the player's 430 skill level, either minor or major deviations from the skeleton 400, 500 are flagged. The processor 200 may find deviations from the skeleton 400, 500 in the base phase 402, 502 of the player's jump shot by comparing the joints of the skeleton 400, 500 to the player's 430 joints. Also, the he computer performing video analysis 102 or 106 may find deviations from the skeleton 400, 500 in the base phase 402, 502 by generating the player skeleton and comparing it to the reference skeleton 400, 500. For example, if the player's 430 shoulders do not match the skeleton's 400, 500 shoulder joints, the player's 430 shoulders may not be square to the basket. The orientation of the player's 430 shoulders may be a result of feet that are not square to the basket. Feet location may also be analyzed. The processor 200 may further analyze how closely the player's limbs and torso match vectors connecting the skeleton's 400, 500 joints. This analysis step is performed on both the front perspective footage and the side perspective footage.

After analyzing the base phase 402, 502 against the base stage skeleton, the computer performing video analysis 102 or 106 repeats steps 606-612 for the other phases of the jump shot. For example, the processor 200 may repeat steps 606-612 for the frame phase 404, the release phase 406, the follow through phase 408, and the finish phase 410.

Figure 12:
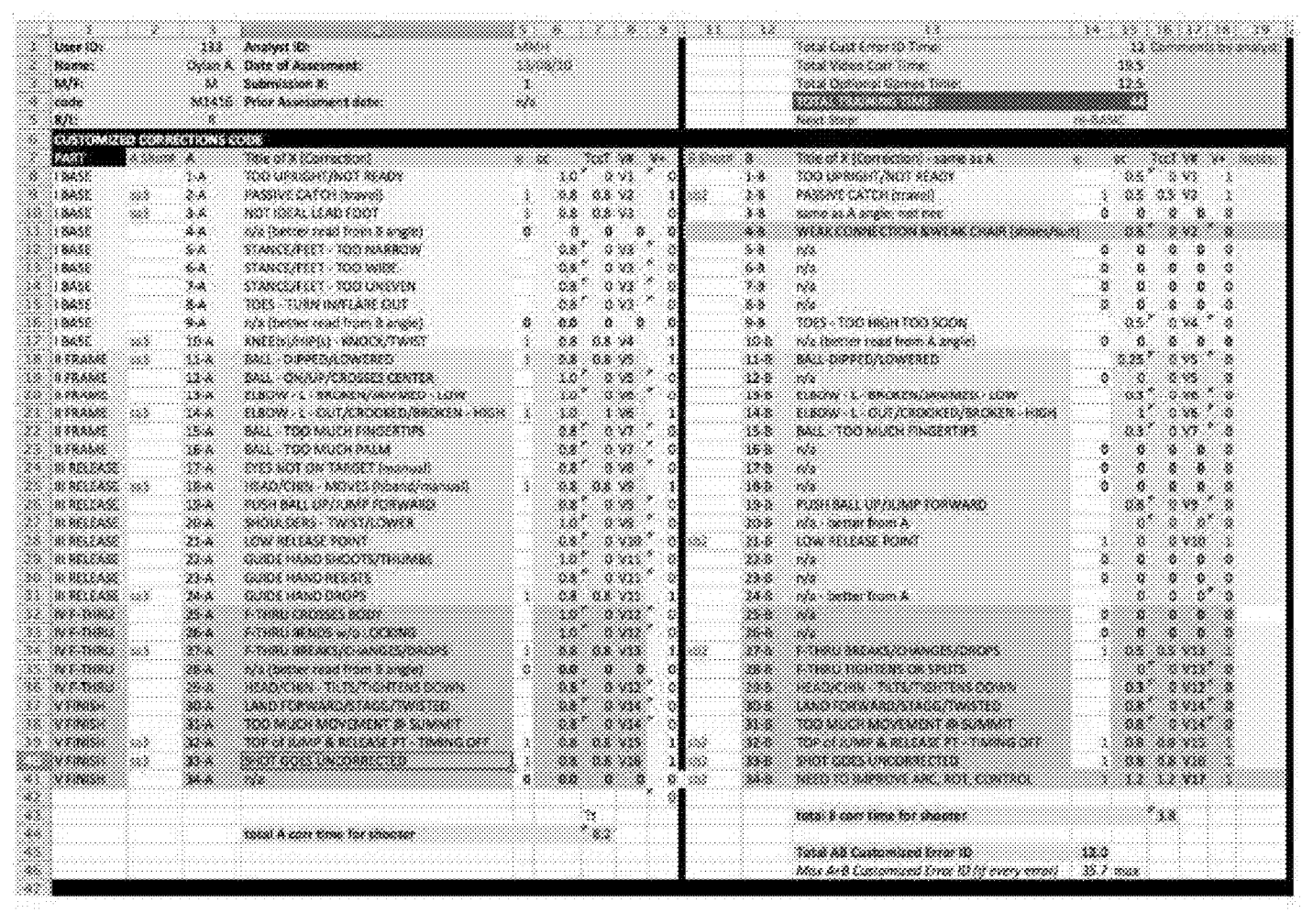

After analyzing all phases of the jump shot, the mobile device 102 uploads the results to the remote server 106 in step 614, and the mobile device 102 also presents the video analysis results to the user on the I/O device 204 in step 616. FIG. 12 illustrates an exemplary results spreadsheet showing all the areas of the jump shot analyzed by the computer performing video analysis 102 or 106.

FIG. 7 illustrates a method 700 for video analysis, whereby the remote server 106 performs video analysis. The method 700 begins in step 702 when the remote server 106 receives video of the player 430 taking a jump shot from the mobile device 102. The mobile device 102 captures the player 430 taking jump shot from two perspectives. Preferably, these perspectives are a front perspective and a side perspective. So, the remote server 106 receives two video clips. Also, preferably, the mobile device 102 is held very still and captures high quality video footage against a still background.

Subsequently, in step 704, the remote server 106 processor 300 determines which frames of the video footage captured by the mobile device 102 camera 206 actually represent the player 430 taking a jump shot. Any video frames not representing the jump shot, such as frames where the player 430 is dribbling, are disregarded. Only frames where the player 430 is taking a jump shot are analyzed. This determining step is performed on both the front perspective footage and the side perspective footage.

After disregarding extra footage, the processor 300 searches the frames depicting the jump shot for a frame best representing the base phase 402, 502 of the jump shot in step 706. For example, the processor 300 finds the frame where the player is lowest in his squat to find the frame representing the base phase 402, 502 of the jump shot. This searching step is performed on both the front perspective footage and the side perspective footage.

After finding the frame depicting the base phase 402, 502, the processor 300 generates a skeleton 400, 500 that matches the player's 430 body measurements in step 708. The method 700 assumes that the remote server 106 has already received the body measurements from the mobile device 102. In the exemplary embodiments, the application 250 on the mobile device 102 may not allow the user to upload video to the remote server 106 until the body measurements have been entered into the mobile device 102. In one embodiment, the mobile device 102 sends player body measurements with the captured video. Alternatively, the remote server 106 may save player body measurements for each player 430.

In step 710, the processor 300 superimposes a base stage 402, 502 of the referenced skeleton 400, 500 onto the frame determined to depict the base phase 402, 502 of the jump shot. This superimposing step is performed on both the front perspective frame and the side perspective frame.

Next, the processor 300 analyzes the player's 430 base phase 402, 502 fundamentals based on the superimposed skeleton 400, 500 in step 712. Depending on the player's 430 skill level, either minor or major deviations from the skeleton 400, 500 are flagged. The processor 200 may find deviations from the skeleton 400, 500 in the base phase 402, 502 of the player's jump shot by comparing the joints of the skeleton 400, 500 to the player's 430 joints. Also, the he computer performing video analysis 102 or 106 may find deviations from the skeleton 400, 500 in the base phase 402, 502 by generating the player skeleton and comparing it to the reference skeleton 400, 500. For example, if the player's 430 shoulders do not match the skeleton's 400, 500 shoulder joints, the player's 430 shoulders may not be square to the basket. The orientation of the player's 430 shoulders may be a result of feet that are not square to the basket. Feet location may also be analyzed. The processor 300 may further analyze how closely the player's limbs and torso match vectors connecting the skeleton's 400, 500 joints. This analysis step is performed on both the front perspective footage and the side perspective footage.

After analyzing the base frame 402, 502 against the base stage skeleton 400, 500, steps 706-712 for the other phases of the jump shot. For example, the processor 300 may complete steps 706-712 for the frame phase 404, the release phase 406, the follow through phase 408, and the finish phase 410.

After analyzing all phases of the jump shot, the remote server 106 saves the results to a database in step 714 and sends the results to the mobile device 102 in step 716. When the remote server 106 sends the results, the remote server 106 may include hyperlinks to training videos to help the player fix the fundamental deviations from the skeleton 400, 500 found by the remote server 106.

As described above, the remote server 106 may perform may tasks other than just video analysis. For example, the remote server 106 may save a video of the player's 430 best shot in the database 308. The player 430 can download that shot at any time to view what they did right and what still needs improvement. The database 308 may save many best shot videos for all players 430 registered with the remote server 106. This best shot practice may be used more frequently by professionals who do not need to improve mechanics, but should simply maintain their method of shooting. For example, the professional player may save their best shot in the database 308, and the computer performing video analysis 102 or 106 may generate a skeleton 400, 500 based on that best shot saved in the database 308. In this way, the professional player may quickly determine what changes in his jump shot he may have developed from his best shot.

Figure 13:
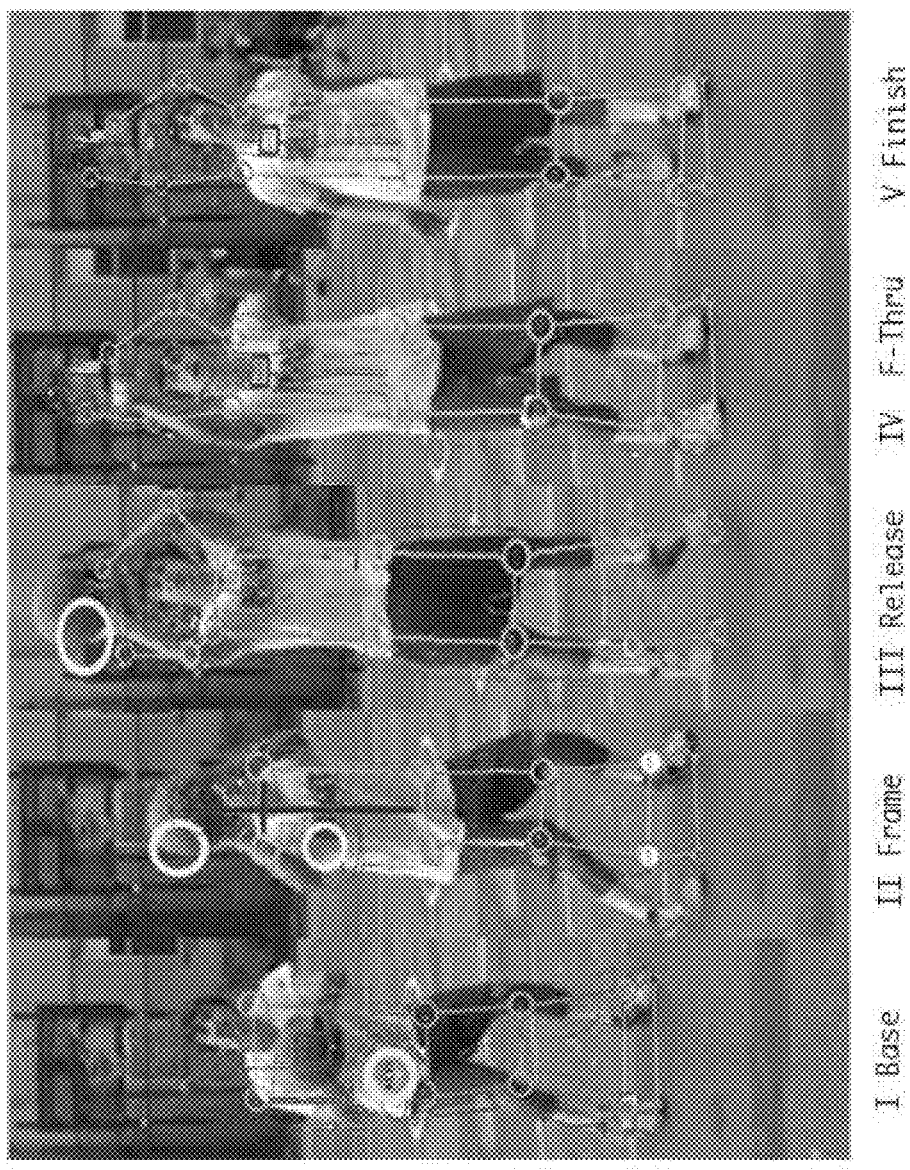
FIG. 13 illustrates a reference skeleton superimposed over video frames of a player taking a jump shot according to an exemplary embodiment.

In addition, the remote server 106 or the mobile device 102 may prepare a video of the player's 430 jump shot with the skeleton 400, 500 superimposed over the video. In this way, the player 430 can see how the computer performing video analysis 102 or 106 determined the deviations from the skeleton 400, 500 reported to the player 430. FIG. 13 illustrates the reference skeleton 400, 500 superimposed over the video.

The remote server 106 may save many videos in the database 308. For example, the database 308 may save one video from each training session, and the player 430 may view past jump shot videos to see the progress he is making. The database 308 may further save progress data. For example, in training session one the remote server 106 may note in the database 308 that the player 430 was not square to the basket. However, in training session ten, the remote server 106 may find that the player 430 was square to the basket. Using these two pieces of information, the remote server 106 may note that the player 430 has made significant progress on a previous issue with his or her jump shot.

The video analysis system 100 may further be configured to detect the ball and a basketball hoop to determine whether the player shot the ball through the hoop. The remote server 106 or the mobile device 102 may further be configured to track the number of made baskets during a training session. The remote server 106 or the mobile device 102 may compile statistics for the player 430 detailing the number of made shots, the number of shots taken, the percentage of shots made, etc.

If the video analysis system 100 is configured to detect whether the ball went through the basketball hoop, the video analysis system 100 may use this outcome data (e.g. whether the ball went through the hoop) and correlate the outcome data with detected deviations from the reference skeleton 400, 500. For example, if a player 430 has a tendency to jump forward on his jump shots, this would show up as a deviation from the reference skeleton 400, 500. But, if the player 430 generally makes most of the shots where he jumps forward, the jumping forward deviation may be a low priority fundamental deviation for the player 430 to work on. As another example, the player 430 may miss 80% of his shots when he leaves his elbow out versus making 70% of his shots when his elbows are properly positioned. So if the video analysis system 100 detects both the jumping forward deviation and the elbow deviation, the video analysis system 100 may only report the elbow deviation to the player 430. In this way, the video analysis system 100 communicates which deviations are outcome determinative, which may be helpful in identifying which aspects of the jump shot the player 430 should focus on. In subsequent training sessions, when the elbow problem has been addressed, the video analysis system 100 may suggest a more balanced jump and less jumping forward.

The video analysis process described herein can easily be performed on other physical activities, such as a golf swing, throwing a football, a baseball swing, a pitching throw, running, or any other physical activity. To apply the exemplary embodiments to other sports or activities, the remote server 106 needs only to receive skeletons for other physical activities. More specifically, the video analysis process may be applied to a volleyball serve, a tennis serve, throwing a football, kicking or punting a football, a golf swing, discus throwing, shot put throwing, track events (high jump, pole vaulting, hurdling, long jumping), or swimming strokes (e.g. back stroke, free style, butterfly, breast stroke). To apply the video analysis process described herein to other physical activities, the system may include different skeletons uploaded to the database 308 based on the various physical activities.

For physical activities other than a jump shot, the remote server 106 or the mobile device 102 may store different skeletons than the jump shot skeleton 400, 500 illustrated in FIGS. 4 and 5. Different physical activities comprise a variety of body movements. For example, a pitching skeleton may include a leg kick, an upright stance, a step forward, and an arm follow through for the pitch delivery. The pitching skeleton may include locations for other "joints," such as glove hand position before delivery, head position during delivery, or any other body positioning. Further, some physical activities may benefit from more than two perspectives of the activity, and so, more than two skeletons may be generated (one for each perspective).

The skeleton-based video analysis process may also be configured to perform injury prevention tests. For example, the system may receive video of a person performing an anterior cruciate ligament (ACL) jump test. During the ACL jump test, a person may jump from a relatively low height (e.g. a chair or bench) and land on the floor. The way the person jumps and lands may indicate weakness in the person's knee ligaments, which may lead to significant injury. The skeleton for the ACL test may illustrate an ideal way to jump and land from a bench. The computer performing video analysis 102 or 106 may look for deviations from the ACL test skeleton. If deviations found have been shown to increase injury, the person may try to correct their jumping and landing style to prevent injury.

Similarly to the ACL test, under-pronation or over-pronation during running, which can lead to serious foot or ankle injuries, may be detected while a person runs. By analyzing video of a person running based on a running skeleton, the computer performing video analysis 102 or 106 may determine whether the person exhibits over-pronation or under-pronation problems. The computer 102 or 106 may then suggest simple injury prevention videos to help the person prevent injury as a result of their over-pronation or under-pronation problems.

In view of the foregoing, it will be seen that the several advantages of the invention are achieved and attained.

The exemplary embodiments can include one or more computer programs that embody the functions described herein and illustrated in the appended flow charts. However, it should be apparent that there could be many different ways of implementing aspects of the exemplary embodiments in computer programming, and these aspects should not be construed as limited to one set of computer instructions. Further, those skilled in the art will appreciate that one or more acts described herein may be performed by hardware, software, or a combination thereof, as may be embodied in one or more computing systems.

The functionality described herein can be implemented by numerous modules or components that can perform one or multiple functions. Each module or component can be executed by a computer, such as a server, having a non-transitory computer-readable medium and processor. In one alternative, multiple computers may be necessary to implement the functionality of one module or component.

Unless specifically stated otherwise as apparent from the following discussion, it is appreciated that throughout the description, discussions utilizing terms such as "determining" or "comparing" or "processing" or the like, can refer to the action and processes of a data processing system, or similar electronic device, that manipulates and transforms data represented as physical (electronic) quantities within the system's registers and memories into other data similarly represented as physical quantities within the system's memories or registers or other such information storage, transmission or display devices.

The exemplary embodiments can relate to an apparatus for performing one or more of the functions described herein. This apparatus may be specially constructed for the required purposes, or it may comprise a general purpose computer selectively activated or reconfigured by a computer program stored in the computer. Such a computer program may be stored in a machine (e.g. computer) readable storage medium, such as, but is not limited to, any type of disk including floppy disks, optical disks, CD-ROMs and magnetic-optical disks, read only memories (ROMs), random access memories (RAMs) erasable programmable ROMs (EPROMs), electrically erasable programmable ROMs (EEPROMs), magnetic or optical cards, or any type of media suitable for storing electronic instructions, and each coupled to a bus.

The exemplary embodiments described herein are described as software executed on at least one server, though it is understood that embodiments can be configured in other ways and retain functionality. The embodiments can be implemented on known devices such as a personal computer, a special purpose computer, cellular telephone, personal digital assistant ("PDA"), a digital camera, a digital tablet, an electronic gaming system, a programmed microprocessor or microcontroller and peripheral integrated circuit element(s), and ASIC or other integrated circuit, a digital signal processor, a hard-wired electronic or logic circuit such as a discrete element circuit, a programmable logic device such as a PLD, PLA, FPGA, PAL, or the like. In general, any device capable of implementing the processes described herein can be used to implement the systems and techniques according to this invention.

It is to be appreciated that the various components of the technology can be located at distant portions of a distributed network and/or the Internet, or within a dedicated secure, unsecured and/or encrypted system. Thus, it should be appreciated that the components of the system can be combined into one or more devices or co-located on a particular node of a distributed network, such as a telecommunications network. As will be appreciated from the description, and for reasons of computational efficiency, the components of the system can be arranged at any location within a distributed network without affecting the operation of the system. Moreover, the components could be embedded in a dedicated machine.

Furthermore, it should be appreciated that the various links connecting the elements can be wired or wireless links, or any combination thereof, or any other known or later developed element(s) that is capable of supplying and/or communicating data to and from the connected elements. The term module as used herein can refer to any known or later developed hardware, software, firmware, or combination thereof that is capable of performing the functionality associated with that element. The terms determine, calculate and compute, and variations thereof, as used herein are used interchangeably and include any type of methodology, process, mathematical operation or technique.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A computer program product for video analysis of a basketball jump shot, the computer program product comprising:
a plurality of processor-executable instructions configured for processing video data, the video data comprising a plurality of frames of a person performing the basketball jump shot, the instructions being resident on a non-transitory computer-readable storage medium and being configured, upon execution by a processor, to:
determine a frame of the video data that depicts a body position of the person in a phase of the basketball jump shot, wherein the phase comprises a member of the group consisting of (1) a base phase, (2) a frame phase, (3) a release phase, (4) a follow-through phase, and (5) a finish phase;
process pixels in the determined frame to determine a body position for the person within the determined frame, wherein the determined body position comprises data indicative of an arrangement of joints and limbs for the person within the determined frame;
receive input indicative of a size and shooting hand for the person;
define a reference skeleton for the basketball jump shot phase in response to the received input such that the reference skeleton is scaled for the person's size and shooting hand;
compare the determined body position in the determined frame with the reference skeleton; and
determine a deviation between the determined body position and the reference skeleton based on the comparison operation.

2. The computer program product of claim 1 wherein the reference skeleton is representative of a desired body position with respect to a fundamental aspect of the basketball jump shot phase, and wherein the deviation is representative of a difference in the fundamental aspect as between the determined body position and the desired body position of the reference skeleton.

3. The computer program product of claim 2, wherein the plurality of processor-executable instructions are further configured to:
perform the frame determination operation, the processing operation, the comparison operation, and the deviation determination operation with respect to a plurality of the basketball jump shot phases.

4. The computer program product of claim 3 wherein the phases comprise at least two members of the group consisting of (1) the base phase, (2) the frame phase, (3) the release phase, (4) the follow-through phase, and (5) the finish phase.

5. The computer program product of claim 3 wherein the phases comprise (1) the base phase, (2) the frame phase, (3) the release phase, (4) the follow-through phase, and (5) the finish phase.

6. The computer program product of claim 2, wherein the plurality of processor-executable instructions are further configured to:
compute an arc of a basketball for the basketball jump shot based on the video data.

7. The computer program product of claim 2, wherein the plurality of processor-executable instructions are further configured to:
compute data indicative of a release rate for the basketball jump shot based on the video data.

8. The computer program product of claim 1, wherein the plurality of processor-executable instructions are further configured to:
repeat the frame determination operation, the processing operation, the comparison operation, and the deviation determination operation for a plurality of basketball jump shots by the person; and
maintain data indicative of whether the basketball jump shots went through a basketball hoop;
build a database associated with the basketball jump shots, the database including the determined deviations for the basketball jump shots and data indicative of which of the basketball jump shots went through the basketball hoop.

9. The computer program product of claim 8, wherein the plurality of processor-executable instructions are further configured to:
analyze the database to generate metrics about the person's basketball jump shots; and
communicate the generated metrics for presentation to a user.

10. The computer program product of claim 8, wherein the plurality of processor-executable instructions are further configured to:
determine a plurality of deviations with respect to a plurality of the basketball jump shots based on the repeated operations; and
analyze the database to correlate the determined deviations for the basketball jump shots with respect to the data indicative of whether the basketball jump shots went through the basketball hoop.

11. The computer program product of claim 10, wherein the plurality of processor-executable instructions are further configured to:
identify which determined deviations exhibit a correlation beyond a threshold with respect to basketball jump shots that did not go through the basketball hoop.

12. The computer program product of claim 1 wherein the plurality of processor-executable instructions are further configured to:
search a plurality of the frames of the video data to identify a frame that exhibits a plurality of characteristics that are representative of the basketball jump shot phase, wherein the identified frame serves as the determined frame.

13. The computer program product of claim 1, wherein the plurality of processor-executable instructions are further configured to:
communicate a result based on the determined deviation.

14. The computer program product of claim 1 wherein the plurality of processor-executable instructions are further configured to:
superimpose the reference skeleton over the determined body position.

15. The computer program product of claim 1 wherein the video data exhibits a perspective with respect to the person.

16. The computer program product of claim 15 wherein the perspective comprises a member of the group consisting of a front view and a side view.

17. The computer program product of claim 1 wherein the plurality of processor-executable instructions are further configured to:
  capture the video data with a camera resident on a mobile computing device.

18. The computer program product of claim 1 wherein the determined frame comprises a plurality of frames that depict the person's body position in the basketball jump shot phase.

19. The computer program product of claim 1, wherein the reference skeleton comprises an image that depicts a plurality joints and lines connecting the joints that are representative of a player in the basketball jump shot phase.

20. The computer program product of claim 1, wherein the reference skeleton comprises a plurality of data points indicating locations of a plurality of joints and limbs relative to each other that are representative of a player in the basketball jump shot phase.

21. The computer program product of claim 1, wherein the plurality of processor-executable instructions are further configured to:
  calculate body edge coordinates and a body size for the person in the basketball jump shot phase based on the processed pixels of the determined frame;
  determine joint coordinates for the person in the basketball jump shot phase based on the body edge coordinates and the body size; and
  perform the comparison based on the determined joint coordinates relative to the reference skeleton.

22. The computer program product of claim 1, wherein the received user input further comprises data indicative of a gender for the person, and wherein the plurality of processor-executable instructions are further configured to scale the reference skeleton for the person's gender.

23. A method for video analysis of a basketball jump shot, the method comprising:
  processing video data, the video data comprising a plurality of frames of a person performing the basketball jump shot, wherein the processing step comprises:
    a processor determining a frame of the video data that depicts a body position of the person in a phase of the basketball jump shot, wherein the phase comprises a member of the group consisting of (1) a base phase, (2) a frame phase, (3) a release phase, (4) a follow-through phase, and (5) a finish phase;
    the processor processing pixels in the determined frame to determine a body position for the person within the determined frame, wherein the determined body position comprises data indicative of an arrangement of joints and limbs for the person within the determined frame;
    the processor comparing the determined body position in the determined frame with a reference skeleton for the phase of the basketball jump shot phase;
    the processor determining a deviation between the determined body position and the reference skeleton based on the comparing step;
  maintaining a database that associates a plurality of different types of deviations for the basketball jump shot phases with data representative of an explanation regarding each deviation type;
  classifying the determined deviation as a deviation type from among a plurality of different types of deviations;
  analyzing the database to map the determined deviation to the explanation data associated with the classified deviation type for the determined deviation; and
  communicating the associated explanation data to a user to facilitate coaching of the person's basketball jump shot.

24. An apparatus for video analysis of a basketball jump shot, the apparatus comprising:
  a processor configured for processing video data, the video data comprising a plurality of frames of a person performing the basketball jump shot, wherein the processor is configured to:
    determine a frame of the video data that depicts a body position of the person in a phase of the basketball jump shot, wherein the phase comprises a member of the group consisting of (1) a base phase, (2) a frame phase, (3) a release phase, (4) a follow-through phase, and (5) a finish phase;
    process pixels in the determined frame to determine a body position for the person within the determined frame, wherein the determined body position comprises data indicative of an arrangement of joints and limbs for the person within the determined frame;
    compare the determined body position in the frame with a reference skeleton for the basketball jump shot phase;
    determine a deviation between the determined body position and the reference skeleton based on the comparison operation;
    repeat the frame determination operation, the processing operation, the comparison operation, and the deviation determination operation for a plurality of basketball jump shots by the person such that a plurality of deviations are determined with respect to a plurality of the basketball jump shots based on the repeated operations, wherein the deviations correspond to a plurality of different types of deviations;
    maintain data indicative of whether the basketball jump shots went through a basketball hoop;
    build a database associated with the basketball jump shots, the database including the determined deviations for the basketball jump shots and data indicative of which of the basketball jump shots went through the basketball hoop;
    analyze the database to correlate the determined deviations for the basketball jump shots with respect to the data indicative of whether the basketball jump shots went through the basketball hoop; and
    classify at least one of the determined deviation types as being an outcome-determinative deviation type based on the correlations of the determined deviations with the data indicative of whether the basketball jump shots went through the basketball hoop.

25. The apparatus of claim 24 wherein the processor is resident on a mobile computing device.

26. The apparatus of claim 24 wherein the processor is resident on a server system.

27. A system comprising:
  a camera configured to generate a plurality of image frames of a person performing a basketball jump shot;
  a memory; and
  a processor for cooperation with the camera and the memory, the processor configured to:
    receive the image frames from the camera;
    process pixels of the image frames to determine and identify which of the image frames is representative of a crest of a jump by the player for the basketball jump shot in the release phase;

process pixels in the identified image frame to determine a body position for the person within the identified image frame, wherein the determined body position comprises data indicative of an arrangement of joints and limbs for the person within the identified frame;

compare the determined body position to a release phase reference body position;

determine whether the person demonstrated a deviation from the release phase reference body position while performing the basketball jump shot as a result of the comparison operation; and in response to a determination that the person demonstrated the deviation, store data representative of the deviation in the memory.

28. The system of claim 27, wherein the processor is further configured to:

process pixels of the identified release phase image frame to determine whether the basketball has already left a shooting hand of the person; and in response to a determination that the basketball had already left the shooting hand, (1) determine that an error corresponding to a release point being too low for the person exists, and (2) communicate the determined error to a user to facilitate coaching of the person's basketball jump shot.

29. The system of claim 27 wherein the camera comprises (1) a first camera configured to generate image frames corresponding to a front view of the person performing the basketball jump shot, and (2) a second camera configured to generate image frames corresponding to a side view of the person performing the basketball jump shot, and wherein the identified image frame includes a front view image frame corresponding to the release phase and a side view image frame corresponding to the release phase.

30. A system comprising:

a camera configured to generate a plurality of image frames of a person performing a basketball jump shot;

a memory; and a processor for cooperation with the camera and the memory, wherein the processor is configured to:
receive the image frames from the camera;
process pixels of the image frames to determine and identify which of the image frames is representative of the player in a frame phrase of the basketball jump shot and preparing to execute the basketball jump shot such that the player is on his or her toes but not yet in the air;
process pixels in the identified image frame to determine a body position for the person within the identified image frame, wherein the determined body position comprises data indicative of an arrangement of joints and limbs for the person within the identified frame;
compare the determined body position with a frame phase reference body position;
determine whether the person demonstrated a deviation from the frame phase reference body position while performing the basketball jump shot based on the comparison operation; and
in response to a determination that the person demonstrated the deviation, store data representative of the deviation in the memory.

31. A system comprising:

a camera configured to generate a plurality of image frames of a person performing a basketball jump shot;

a memory; and a processor for cooperation with the camera and the memory, wherein the processor is configured to:
receive the image frames from the camera;
process pixels of the image frames to identify an image frame that depicts the person in a frame phase of the basketball jump shot;
process pixels in the identified image frame to determine a body position for the person within the identified image frame, wherein the determined body position comprises data indicative of an arrangement of joints and limbs for the person within the identified frame;
compare the determined body position with a frame phase reference body position;
determine based on the comparison whether the elbow corresponding to the player's shooting hand is flared out relative to the frame phase reference body position; and
in response to a determination that the elbow corresponding to the player's shooting hand is flared out relative to the frame phase reference body position, (1) determine that an error corresponding to an elbow flare out exists, (2) store data representative of the error in the memory, and communicate the determined error to a user to facilitate coaching of the person's basketball jump shot.

32. The system of claim 31 wherein the camera comprises (1) a first camera configured to generate image frames corresponding to a front view of the person performing the basketball jump shot, and (2) a second camera configured to generate image frames corresponding to a side view of the person performing the basketball jump shot, and wherein the identified image frame includes a front view image frame corresponding to the frame phase and a side view image frame corresponding to the frame phase.

33. A computer program product for video analysis of a basketball jump shot, the computer program product comprising:

a plurality of processor-executable instructions configured for processing video data, the video data comprising a plurality of frames of a person performing the basketball jump shot, the instructions being resident on a non-transitory computer-readable storage medium and being configured, upon execution by a processor, to:
determine a frame of the video data that depicts a body position of the person in a phase of the basketball jump shot, wherein the phase comprises a member of the group consisting of (1) a base phase, (2) a frame phase, (3) a release phase, (4) a follow-through phase, and (5) a finish phase;
process pixels in the determined frame to determine a body position for the person within the determined frame, wherein the determined body position comprises data indicative of an arrangement of joints and limbs for the person within the determined frame;
compare the determined body position in the determined frame with a reference skeleton for the basketball jump shot phase;
determine a deviation between the determined body position and the reference skeleton based on the comparison operation;

maintain a database that associates a plurality of different types of deviations for the basketball jump shot phases with data representative of an explanation regarding each deviation type;

classify the determined deviation as a deviation type from among a plurality of different types of deviations;

analyze the database to map the determined deviation to the explanation data associated with the classified deviation type for the determined deviation; and communicate the associated explanation data to a user to facilitate coaching of the person's basketball jump shot.

34. The computer program product of claim 33 wherein the instructions are configured for execution by a mobile computing device.

35. The computer program product of claim 33 wherein the instructions are configured for execution by a server system.

36. The computer program product of claim 33, wherein the plurality of processor-executable instructions are further configured to:

perform the frame determination operation, the processing operation, the comparison operation, and the deviation determination operation with respect to first video data from a first perspective and second video data from a second perspective.

37. The computer program product of claim 33 wherein the processor-executable instructions comprise a first plurality of the processor-executable instructions configured for execution by a first processor and a second plurality of the processor-executable instructions configured for execution by a second processor.

38. The computer program product of claim 33 wherein the deviation types comprise a plurality of members of the group consisting of (1) a release point too low deviation type, (2) a too upright without enough knee bend and squat deviation type, (3) an imbalance deviation type, (4) an elbow flare out deviation type, (5) a misplaced guide hand deviation type, (6) a falling backward deviation type, (7) a landing forward deviation type, and (8) a not square deviation type.

39. A computer program product for video analysis of a basketball jump shot, the computer program product comprising:

a plurality of processor-executable instructions configured for processing video data, the video data comprising a plurality of frames of a person performing the basketball jump shot, the instructions being resident on a non-transitory computer-readable storage medium and being configured, upon execution by a processor, to:

determine a frame of the video data that depicts a body position of the person in a phase of the basketball jump shot, wherein the phase comprises a member of the group consisting of (1) a base phase, (2) a frame phase, (3) a release phase, (4) a follow-through phase, and (5) a finish phase;

process pixels in the determined frame to determine a body position for the person within the determined frame, wherein the determined body position comprises data indicative of an arrangement of joints and limbs for the person within the determined frame;

compare the determined body position in the determined frame with a reference skeleton for the basketball jump shot phase; and determine a deviation between the determined body position and the reference skeleton based on the comparison operation;

repeat the frame determination operation, the processing operation, the comparison operation, and the deviation determination operation for a plurality of basketball jump shots by the person such that a plurality of deviations are determined with respect to a plurality of the basketball jump shots based on the repeated operations, wherein the deviations correspond to a plurality of different types of deviations;

maintain data indicative of whether the basketball jump shots went through a basketball hoop;

build a database associated with the basketball jump shots, the database including the determined deviations for the basketball jump shots and data indicative of which of the basketball jump shots went through the basketball hoop;

analyze the database to correlate the determined deviations for the basketball jump shots with respect to the data indicative of whether the basketball jump shots went through the basketball hoop; and classify at least one of the determined deviation types as being an outcome-determinative deviation type based on the correlations of the determined deviations with the data indicative of whether the basketball jump shots went through the basketball hoop.

40. A computer program product for video analysis of a basketball jump shot, the computer program product comprising:

a plurality of processor-executable instructions configured for processing video data, the video data comprising a plurality of frames of a person performing the basketball jump shot, the instructions being resident on a non-transitory computer-readable storage medium and being configured, upon execution by a processor, to:

determine a frame of the video data that depicts a body position of the person in a phase of the basketball jump shot, wherein the phase comprises a member of the group consisting of (1) a base phase, (2) a frame phase, (3) a release phase, (4) a follow-through phase, and (5) a finish phase;

process pixels in the determined frame to determine a body position for the person within the determined frame, wherein the determined body position comprises data indicative of an arrangement of joints and limbs for the person within the determined frame;

receive input indicative of a skill level for the person;

compare the determined body position in the determined frame with a reference skeleton for the basketball jump shot phase;

compute data representative of a difference between the body position in the frame and the reference skeleton in response to the comparison between the body position in the frame and the reference skeleton for the basketball jump shot phase;

compare the computed data with a threshold that is scaled based on the skill level input; and in response to a determination that the computed data exceeds the threshold, classify the difference as a deviation between the determined body position and the reference skeleton.

* * * * *